(12) United States Patent
Huebner et al.

(10) Patent No.: US 6,538,118 B1
(45) Date of Patent: Mar. 25, 2003

(54) EXPRESSION OF LIPOPROTEINS

(75) Inventors: Robert C. Huebner, Stroudsburg, PA (US); Lorne F. Erdile, Stroudsburg, PA (US); Donald J. Warakomski, Jr., Tannersville, PA (US); Robert S. Becker, Henryville, PA (US); Maryann B. Gray, Bartonsville, PA (US); Derek J. Pyle, East Stroudsburg, PA (US)

(73) Assignee: Connaught Laboratories, Inc., Swiftwater, PA (US)

( * ) Notice: Subject to any disclaimer, the term of this patent is extended or adjusted under 35 U.S.C. 154(b) by 0 days.

(21) Appl. No.: 09/067,453

(22) Filed: Apr. 28, 1998

Related U.S. Application Data

(63) Continuation of application No. 08/475,781, filed on Jun. 7, 1995, now abandoned.

(51) Int. Cl.[7] .................. C07H 21/04; C07H 21/02; C12N 15/63; C12N 15/00; C12N 15/70
(52) U.S. Cl. .................. 536/23.1; 536/23.4; 536/23.7; 435/69.1; 435/69.7; 435/172.3; 435/320.1
(58) Field of Search ................. 536/23.1, 23.7, 536/23.4; 435/69.1, 69.7, 172.3, 320.1

(56) References Cited

U.S. PATENT DOCUMENTS

| | | | |
|---|---|---|---|
| 4,624,926 A | | 11/1986 | Ioyue et al. |
| 4,683,202 A | | 7/1987 | Mullis |
| 4,721,617 A | | 1/1988 | Johnson |
| 4,800,159 A | | 1/1989 | Mullis et al. |
| 4,879,213 A | | 11/1989 | Fox et al. |
| 4,952,496 A | | 8/1990 | Studier et al. |
| 5,476,929 A | * | 12/1995 | Briles et al. |
| 5,583,038 A | * | 12/1996 | Stover |
| 5,679,768 A | * | 10/1997 | Briles et al. |
| 5,728,387 A | * | 3/1998 | Briles et al. |
| 5,753,463 A | * | 5/1998 | Briles et al. |
| 5,804,193 A | * | 9/1998 | Briles et al. |
| 5,856,170 A | * | 1/1999 | Briles et al. |
| 5,871,943 A | * | 2/1999 | Briles et al. |
| 5,965,141 A | * | 10/1999 | Briles et al. |
| 5,965,400 A | * | 10/1999 | Briles et al. |
| 5,980,909 A | * | 11/1999 | Briles et al. |
| 5,997,882 A | * | 12/1999 | Briles et al. |
| 6,024,963 A | * | 2/2000 | Becker et al. |
| 6,027,734 A | * | 2/2000 | Briles et al. |
| 6,042,838 A | * | 3/2000 | Briles et al. |
| 6,054,296 A | * | 4/2000 | Bergström et al. |
| 6,143,872 A | * | 11/2000 | Barbour et al. |
| 6,203,798 B1 | * | 3/2001 | Bergstrom et al. |
| 6,204,018 B1 | * | 3/2001 | Bergstrom et al. |
| 6,248,581 B1 | * | 6/2001 | Gicquel et al. |
| 6,368,603 B1 | * | 4/2002 | Jarecki-Black ............ 424/234.1 |
| 6,379,675 B1 | * | 4/2002 | Becker et al. ............ 424/234.1 |

FOREIGN PATENT DOCUMENTS

| | | |
|---|---|---|
| CA | 2001328 | 4/1991 |
| CA | 2032914 | 6/1991 |
| CA | 2025178 | 7/1991 |
| EP | 055 942 | 6/1988 |
| EP | 055 560 | 1/1993 |
| EP | 0522560 | * 1/1993 |
| EP | 0622081 | * 11/1994 |
| WO | WO 90/04411 | 5/1990 |
| WO | WO 91/09870 | 7/1991 |
| WO | WO 91/09952 | 7/1991 |
| WO | WO 91/13096 | 9/1991 |
| WO | WO 91/13630 | 9/1991 |
| WO | WO 92/00055 | 1/1992 |
| WO | WO 92/14488 | 9/1992 |
| WO | WO 93/07897 | 4/1993 |
| WO | WO 96/10214 | 5/1993 |
| WO | WO 93/08306 | 6/1993 |
| WO | WO96 40290 | * 12/1996 |
| WO | WO96 40718 | * 12/1996 |

OTHER PUBLICATIONS

Steere et al, NEJM, 339/4:209–215, 1998.*
Sigal et al, NEJM, 339/4:216–222, 1998.*
Keller et al, JAMA, Jun. 8, 1994, 271/22:1764–68.*
Simon et al, J. Infectious Diseases, 1991, 164:123–32.*
Fikrig et al., (1990) *Science*, vol. 250, pp. 553–556.
Simon et al., (1991) *J. Infect. Dis.*, vol. 164, pp. 123–132.
Dunn et al., (1990) *Protein Expression and Purification*, vol. 1, pp. 159–168.
Bessler et al., (1985) *Immunobiology*, vol. 170, pp. 239–244.
Biesert et al., (1987) *Eur. J. Biochem.*, vol. 162, pp. 651–657.
Deres et al., (1989) *Nature*, vol. 342, pp. 561–564.
Brandt et al., (1990) *Infection and Immunity*, vol. 58, pp. 983–991.
Fikrig et al., (1992) *Infection and Immunity*, vol. 60, pp. 773–777.
Fikrig et al., (1991) *J. Infect. Dis.*, vol. 164, pp. 1224–1227.
Jonsson et al., (1992) *Infect. Immun.*, vol. 60, pp. 1845–1853.
Gondolf et al., (1990) *J. Chromatography*, vol. 521, pp. 325–334.
Barbour et al., (1985) *The Journal of Infectious Diseases*, vol. 152, pp. 478–484.
Wallich et al., (1989) *Nucleic Acids Research*, vol. 17, pp. 8864.
Radolf et al., (1988) *Infect. and Immunity*, vol. 56, pp. 490–498.

(List continued on next page.)

*Primary Examiner*—Nita Minnifield
(74) *Attorney, Agent, or Firm*—Patrick J. Halloran

(57) ABSTRACT

Heterologous lipidated proteins formed recombinantly are disclosed and claimed. The expression system can be *E. coli*. The heterologous lipidated protein has a leader sequence which does not naturally occur with the protein portion of the lipidated protein. The lipidated protein can have the Borrelia OspA leader sequence. The protein portion can be OspC, PspA, UreA, Ure B, or a fragment thereof. Methods and compositions for forming and employing the proteins are also disclosed and claimed.

10 Claims, 15 Drawing Sheets

OTHER PUBLICATIONS

Howe et al., (1986) *Infect. and Immunity*, vol. 54, pp. 207–212.
Crabtree et al., (1984) *Journal of Bacteriology*, vol. 158, pp. 354–356.
Studier et al., (1990) *Method in Enzymology*, vol. 185, pp. 60–89.
Bergstrom et al., (1989) *Molecular Microbiology*, vol. 3, pp. 479–486.
Benach et al., (1988) *Journal of Immunology*, vol. 140, pp. 265–272.
Simon et al., (1991) *Immunology Today*, vol. 12, pp. 11–16.
Philipp et al., (1993) *Infection and Immunity*, vol. 61, pp, 3047–3059.
Hughes et al., (1993) *Infection and Immunity*, vol. 61, pp. 5115–5122.
Edelman et al., (1991) *Vaccine*, vol. 9, pp. 531–532.
Seeburg et al., (1978) *Nature*, vol. 276, pp. 795–798.
Tacon et al., (1980) *Molec. Gen. Genet.*, vol. 177, pp. 427–438.
Ghrayeb et al., (1984) *The Journal of Biological Chemistry*, vol. 259, pp. 463–467.
Yu et al., (1984) *The Journal of Biological Chemistry*, vol. 259, pp. 6013–6018.
Pugsley et al., (1985) *FEMS Microbiology Reviews*, vol. 32, pp. 3–38.
Wu et al., (1986) *Current Topics in Microbiology and Immunology*, vol. 125, pp. 127–157.
Klein et al., (1988) *Protein Engineering*, vol. 2, pp. 15–20.
Heijne et al., (1989) *Protein Engineering*, vol. 2, pp. 531–534.
Rioux et al., (1992) *Gene*, vol. 116, pp. 13–20.
Lunn et al., (1986) *Current Topics in Microbiology and Immunology*, vol. 125, pp. 59–74.
Fuchs et al., (1992) *Molecular Microbiology*, vol. 6, pp. 503–509.
Langerman et al., (1994) *J. Exp. Med.*, vol. 180, pp. 2277–2286.
Bouinoins et al., (1991) *Mol. Microbiology*, vol. 5, pp. 2611–2616.
Bessler et al., (1992) *The 44$^{th}$ Forum in Immunology*, pp. 548.
Briles et al., (1988) *Rev. of Infectious Diseases*, vol. 10, pp. 372–374.
Erdile et al., (1993) *Infection and Immunity*, vol. 61, pp. 81–90.
Keller et al., (1994) *JAMA*, vol. 271, pp. 1764–1768.
McDaniel et al., (1986) *Microbial Pathogenesis*, vol. 1, pp. 519–531.
McDaniel et al., (1991) *Infection and Immunity*, vol. 59, pp. 222–228.
McDaniel et al., (1992) *Microbial Pathogenesis*, vol. 13, pp. 261–269.
McGhee et al., (1993) *Infectious Agents and Disease*, vol. vol. 2, pp. 55–73.
Mestecky, (1987) *Journal of Clinical Immunology*, vol. 7, pp. 265–276.
Preac–Murisc, (1992) *Infection*, vol. 6, pp. 342–349.
Probert et al., (1994) *Infection and Immunity*, vol. 62, pp. 1920–1926.
Ralph et al., (1994) *Annals New York Academy of Sciences*, vol. 730, pp. 361–363.
Sampson et al., (1994) *Infection and Immunity*, vol. 62, pp. 319–324.
Yother et al., (1992) *Journal of Bacteriology*, vol. 174, pp. 601–609.
Burgess et al., (1990) *J. Cell Bid.*, vol. 111, pp. 2129–2138.
Lazar et al., (1988) *Mol. Cell Biol.*, vol. 8, pp. 1247–1252.
Ferrero, (1994) *Infection and Immunity*, vol. 62, pp. 4981–4989.
Scopes, (1987) *Protein Purification: Principles and Practice 2d. Ed.*, pp. 100–126.
Bessler et al., (1992) *Forum in Immunology*, pp. 548.

* cited by examiner

-Suspend cells in PBS

-Freeze/thaw to effect cell lysis

-OspC-L extracted with 0.3% Triton X-114

-Loaded onto DEAE-Sepharose CL 6B column

-OspC-L in column flowthrough

- DEAE-Sepharose flowthrough to pH 4.3 with 1M citric acid

-Loaded onto S-Sepharose fast flow column

-OspC-L binds to column under these conditions

-Wash column with pH 5.5 buffer

-Elute OspC-L with pH 6.0 buffer

FIG. 4

-Suspend cells in lysis buffer

↓ stir 20' R.T.

-Add Triton X-100 to 1% to effect cell lysis

↓ stir 20' R.T.

-Add NaCl to 1M final concentration

↓ stir 20' R.T.

-Centrifuge at 20,000 x g, 30 min.

-Dialyze supernatant vs. 50mM TRIS, pH 8
                                                 2mM EDTA

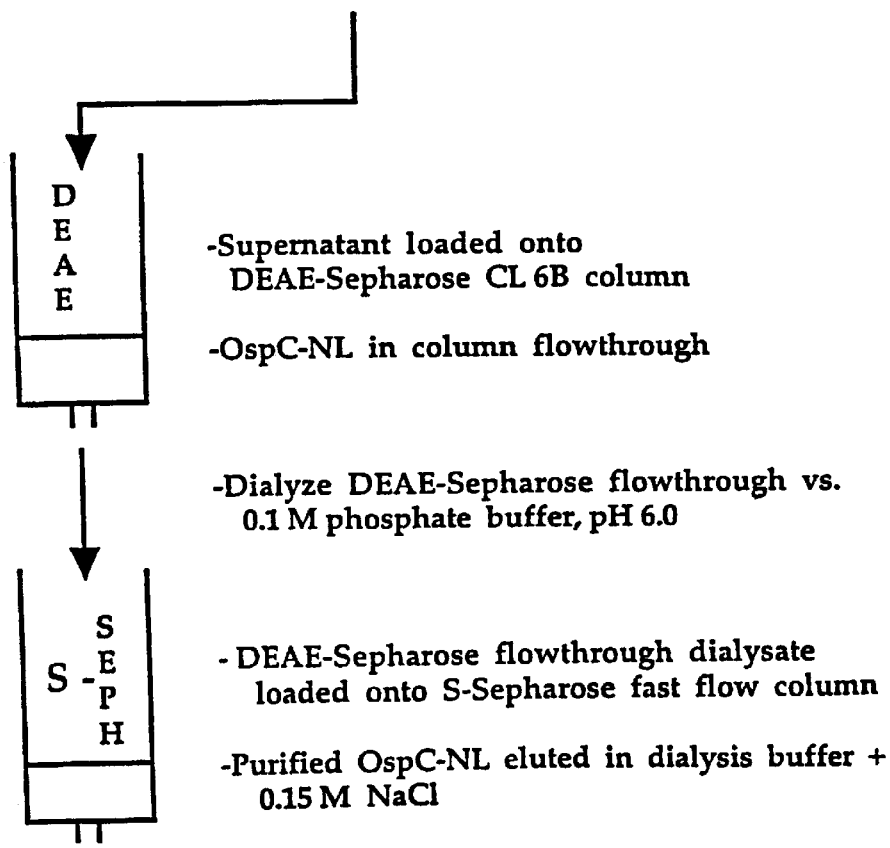

-Supernatant loaded onto
  DEAE-Sepharose CL 6B column

-OspC-NL in column flowthrough

-Dialyze DEAE-Sepharose flowthrough vs.
  0.1 M phosphate buffer, pH 6.0

-DEAE-Sepharose flowthrough dialysate
  loaded onto S-Sepharose fast flow column -Purified OspC-NL eluted in dialysis buffer +
  0.15 M NaCl 1 - Low molecular weight standards
2 - OspC-L/BL21 lysate
3 - OspC-L/BL21 detergent phase
4 - OspC-L/BL21 DEAE flow through/wash pool
5 - OspC-L/BL21 S-Sepharose flow through
6 - OspC-L/BL21 S-Sepharose wash
7 - OspC-L/BL21 S-Sepharose elutant pH 5.5
8 - OspC-L/BL21 S-Sepharose elutant pH 6.0
9 - OspC-L/BL21 S-Sepharose elutant pH 7.5
10 - OspC-L/BL21 S-Sepharose elutant pH 5.7
11 - OspC-L/BL21 S-Sepharose elutant pH 7.5

1 - OspC-NL/JM109 T= 0
2 - OspC-NL/JM109 T= 3 hours
3 - OspC-NL/JM109 DEAE flow through/wash pool
4 - Low molecular weight standards
5 - OspC-NL/JM109 S-Sepharose load
6 - OspC-NL/JM109 S-Sepharose flow through
7 - OspC-NL/JM109 S-Sepharose wash
8 - OspC-NL/JM109 S-Sepharose elutant 150 mM NaCl
9 - OspC-NL/JM109 S-Sepharose elutant 500 mM NaCl -Suspend cells in PBS -Freeze/thaw to effect cell lysis -Cell lysate is centrifuged; cell supernant is saved

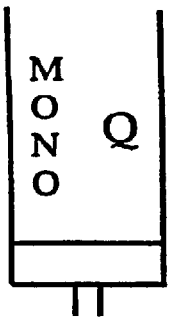

-Loaded onto a MonoQ column at pH 7.5

-Column is washed with loading buffer (50mM Tris 2mM EDTA 10mM NaCL pH 7.5)

-Column is washed with loading buffer containing 100mM NaCl

-PA321-NL is eluted with loading buffer containing 200mM NaCl

-Remaining contaminants are removed with loading buffer containing 1M NaCl

PURIFICATION OF PA321-NL

PA321-L Purification Fractions

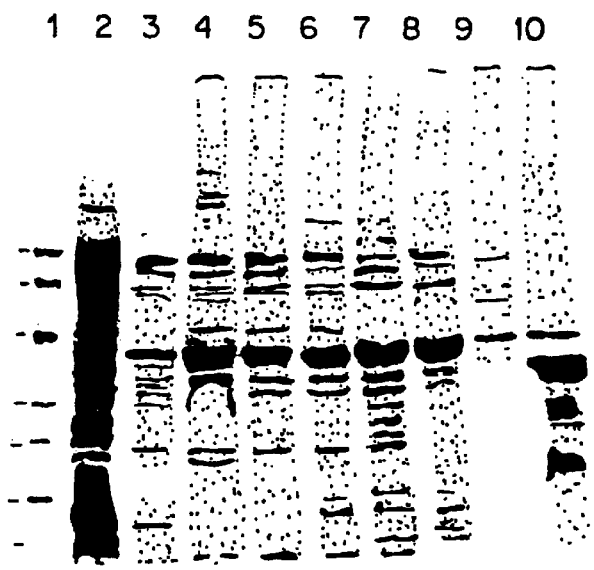

1. Prestained low molecular weight standards (106, 80, 49.5, 32.5, 27.5, and 18.5 kDa)
2. PA321-L/BL21(DE3)pLysS; T = 0
3. PA321-L/BL21(DE3)pLysS; T = 1 hour after IPTG addition
4. PA321-L/BL21(DE3)pLysS; T = 2 hours after IPTG addition
5. PA321-L/BL21(DE3)pLysS; T = 3 hours after IPTG addition
6. PA321-L/BL21(DE3)pLysS; T = 4 hours after IPTG addition
7. PA321-L/BL21(DE3)pLysS; cell lysate
8. PA321-L/BL21(DE3)pLysS; Aqueous phase
9. PA321-L/BL21(DE3)pLysS; Detergent phase
10. PA321-L/BL21(DE3)pLysS; pellet

PA321-NL Purification Fractions

1. Prestained broad molecular weight standards (200, 118, 78, 47.1, 31.4, 25.5, 18.8 and 8.3 kDa)
2. PA321-NL/BL21(DE3)pLysS; T = 0
3. PA321-NL/BL21(DE3)pLysS; T = 1 hour after IPTG addition
4. PA321-NL/BL21(DE3)pLysS; T = 2 hours after IPTG addition
5. PA321-NL/BL21(DE3)pLysS; T = 3 hours after IPTG addition
6. PA321-NL/BL21(DE3)pLysS; cell lysate
7. PA321-NL/BL21(DE3)pLysS; cell supernant and pellet wash pool
8. PA321-NL/BL21(DE3)pLysS; pellet

PA321-NL and PA321-L Purification Samples

1. Prestained broad molecular weight standards (200, 118, 78, 47.1, 31.4, 25.5, 18.8, and 8.3 kDa)
2. PA321-NL MonoQ 0.2M NaCl eluent, lot# 354A-146
3. PA321-NL MonoQ 0.2M NaCl eluent, lot# 354A-147
4. PA321-L Q-sepharose pH 4.0 flow through, lot# 354A-148
5. PA321-L Q-sepharose pH 4.0 flow through, lot# 354A-150

EXPRESSION OF LIPOPROTEINS

REFERENCE TO RELATED APPLICATIONS

This is a continuation of application Ser. No. 08/475,781, filed Jun. 7, 1995, abandoned.

Reference, especially with respect to recombinant Borrelia proteins, is made to U.S. application Ser. No. 08/373,455, filed Jan. 17, 1995, which was a continuation of U.S. application Ser. No. 07/973,338, filed Oct. 29, 1992; International App. No. PCT/US92/08697, filed Oct. 16, 1992 (published as WO 93/08299 on Apr. 29, 1993, and claimed the benefit of U.S. application Ser. No. 07/888,765, filed May 27, 1992, and U.S. application Ser. No. 07/779,048, filed Oct. 18, 1991); and U.S. application Ser. No. 08/211,891, filed Oct. 16, 1992, as the U.S. National Phase of PCT/US92/08697.

Reference, especially with respect to structural genes of pneumococcal proteins, epitopic regions thereof, and administration of pneumococcal proteins, is made to U.S. application Ser. No. 08/214,164, filed Mar. 17, 1994, now U.S. Pat. No. 5,728,387, which was a continuation of U.S. application Ser. No. 07/656,773, filed Feb. 15, 1991, now abandoned; U.S. application Ser. No. 07/835,698, filed Feb. 12, 1992, now abandoned, which was a continuation-in-part of said U.S. application Ser. Nos. 07/656,773; 08/469,434, filed Jun. 6, 1995, now U.S. Pat. No. 5,753,463, which was a continuation of U.S. application Ser. No. 08/072,065, filed Jun. 3, 1993, now abandoned, which was a division of said U.S. application Ser. Nos. 07/835,698; 08/072,070, filed Jun. 3, 1993, now U.S. Pat. No. 5,476,929, which was a division of said U.S. application Ser. Nos. 07/835,698; 08/214,222, filed Mar. 17, 1994, now U.S. Pat. No. 5,804,193, which was a division of said U.S. application Ser. Nos. 07/835,698; 08/468,718, filed Jun. 6, 1995, now U.S. Pat. No. 5,871,943, which was a continuation of Ser. No. 08/072,068, filed Jun. 3, 1993, now abandoned, which was in turn a division of said U.S. application Ser. Nos. 07/835,698; 08/467,852, filed Jun. 6, 1995, now U.S. Pat. No. 5,856,170, which was a continuation of Ser. No. 08/247,491, filed May 23, 1994, now U.S. Pat. No. 5,965,400, which was in turn a continuation of said U.S. application Ser. Nos. 07/835,698; 08/465,746, filed Jun. 6, 1995, now U.S. Pat. No. 5,679,768, which was a continuation of Ser. No. 08/048,896, filed Apr. 20, 1993, now abandoned, which was in turn a continuation-in-part of said U.S. application Ser. Nos. 07/835,698; 08/468,985, filed Jun. 6, 1995, now U.S. Pat. No. 5,997,882, which was a continuation of Ser. No. 08/319,795, filed Oct. 7, 1994, now U.S. Pat. No. 5,980,909, which was in turn a continuation-in-part of U.S. application Ser. No. 08/246,636, filed May 20, 1994, now U.S. Pat. No. 5,965,141, which was in turn a continuation-in-part of said U.S. application Ser. Nos. 08/048,896; and 08/446,201, filed May 19, 1995, now U.S. Pat. No. 6,042,838, which was a continuation-in-part of U.S. application Ser. No. 08/312,949, filed Sep. 30, 1994, now U.S. Pat. No. 6,027,734, which was in turn a continuation-in-part of said U.S. application Ser. No. 08/246,636.

Each of the aforementioned applications is hereby incorporated herein by reference.

FIELD OF THE INVENTION

The present invention is concerned with genetic engineering to effect expression of lipoproteins from vectors containing nucleic acid molecules encoding the lipoproteins. More particularly, the present invention relates to expression of a recombinant lipoprotein wherein the lipidation thereof is from expression of a first nucleic acid sequence and the protein thereof is from expression of a second nucleic acid sequence, the first and second nucleic acid sequences, which do not naturally occur together, being contiguous. The invention further relates to expression of such lipoproteins wherein the first nucleic acid sequence encodes a Borrelia lipoprotein leader sequence. The invention also relates to recombinant lipidated proteins expressed using the nucleic acid sequence encoding the OspA leader sequence, methods of making and using the same compositions thereof and methods of using the compositions. The invention additionally relates to nucleic acid sequences encoding the recombinant lipoproteins, vectors containing and/or expressing the sequences, methods for expressing the lipoproteins and methods for making the nucleic acid sequences and vectors; compositions employing the lipoproteins, including immunogenic or vaccine compositions, such compositions preferably having improved immunogenicity; and methods of using such compositions to elicit an immunological or protective response.

Throughout this specification, various documents are referred to in order to more fully describe the state of the art to which this invention pertains. These documents are each hereby incorporated herein by reference.

BACKGROUND OF THE INVENTION

Lyme borreliosis is the most prevalent tick-borne disease in the United States as well as one of the most important tick-borne infectious diseases worldwide. The spirochete *Borrelia burgdorferi* is the causative agent for Lyme disease. Infection with *B. burgdorferi* produces local and systemic manifestations. Local symptoms that appear early after infection are a skin lesion at the site of the tick bite, termed erythema migrans. Weeks to months after infection, systemic manifestations that include rheumatic, cardiac and neurological symptoms appear. The early local phase of *B. burgdorferi* infection is easily treatable with antibiotics. However, the later systemic phases have proved to be more refractory to antibiotics.

Substantial effort has been directed toward the development of a vaccine for Lyme disease. Two distinct approaches have been used for vaccine development. One approach is to use a vaccine composed of whole inactivated spirochetes, as described by Johnson in U.S. Pat. No. 4,721,617. A whole inactivated vaccine has been shown to protect hamsters from challenge and has been licensed for use in dogs.

Due to the concerns about cross-reactive antigens within a whole cell preparation, human vaccine research has focused on the identification and development of non-cross-reactive protective antigens expressed by *B. burgdorferi*. Several candidate antigens have been identified to date. Much of this effort has focused on the most abundant outer surface protein of *B. burgdorferi*, namely outer surface protein A (OspA), as described in published PCT patent application WO 92/14488, assigned to the assignee hereof. Several versions of this protein have been shown to induce protective immunity in mouse, hamster and dog challenge studies. Clinical trials in humans have shown the formulations of OspA to be safe and immunogenic in humans [Keller et al., JAMA (1994) 271:1764–1768]. Indeed, one formulation containing recombinant lipidated OspA as described in the aforementioned WO 92/14488, is now undergoing Phase III safety/efficacy trials in humans.

While OspA is expressed in the vast majority of clinical isolates of *B. burgdorferi* from North America, a different picture has emerged from examination of the clinical Borrelia isolates in Europe. In Europe, Lyme disease is caused by three genospecies of Borrelia, namely *B. burgdorferi, B. garinii* and *B. afzelli*. In approximately half of the European isolates, OspA is not the most abundant outer surface protein. A second outer surface protein C (OspC) is the major surface antigen found on these spirochetes. In fact, a number of European clinical isolates that do not express OspA have been identified. Immunization of gerbils and mice with purified recombinant OspC produces protective immunity to *B. burgdorferi* strains expressing the homologous OspC protein [V. Preac-Mursic et al., INFECTION (1992) 20:342–349; W. S. Probert et al., INFECTION AND IMMUNITY (1994) 62:1920–1926]. The OspC protein is currently being considered as a possible component of a second generation Lyme vaccine formulation.

Recombinant proteins are promising vaccine or immunogenic composition candidates, because they can be produced at high yield and purity and manipulated to maximize desirable activities and minimize undesirable ones. However, because they can be poorly immunogenic, methods to enhance the immune response to recombinant proteins are important in the development of vaccines or immunogenic compositions.

A very promising immune stimulator is the lipid moiety N-palmitoyl-S-(2RS)-2,3-bis-(palmitoyloxy)propyl-cysteine, abbreviated $Pam_3Cys$. This moiety is found at the amino terminus of the bacterial lipoproteins which are synthesized with a signal sequence that specifies lipid attachment and cleavage by signal peptidase II. Synthetic peptides that by themselves are not immunogenic induce a strong antibody response when covalently coupled to $Pam_3Cys$ [Bessler et al., Research Immunology (1992) 143:548–552].

In addition to an antibody response, one often needs to induce a cellular immune response, particularly cytoxic T lymphocytes (CTLs). $Pam_3Cys$-coupled synthetic peptides are extremely potent inducers of CTLs, but no one has yet reported CTL induction by large recombinant lipoproteins.

The nucleic acid sequence and encoded amino acid sequence for OspA are known for several *B. burgdorferi* clinical isolates and is described, for example, in published PCT application WO 90/04411 (Symbicom AB) for B31 strain of *B. burgdorferi* and in Johnson et al., Infect. Immun. 60:1845–1853 for a comparison of the ospA operons of three *B. burgdorferi* isolates of different geographic origins, namely B31, ACA1 and Ip90.

As described in WO 90/04411, an analysis of the DNA sequence for the B31 strain shows that the OspA is encoded by an open reading frame of 819 nucleotides starting at position 151 of the DNA sequence and terminating at position 970 of the DNA sequence (see FIG. 1 therein). The first sixteen amino acid residues of OspA constitute a hydrophobic signal sequence of OspA. The primary translation product of the full length *B. burgdorferi* gene contains a hydrophobic N-terminal signal sequence which is a substrate for the attachment of a diacyl glycerol to the sulfhydryl side chain of the adjacent cysteine residue. Following this attachment, cleavage by signal peptidase II and the attachment of a third fatty acid to the N-terminus occurs. The complete lipid moiety is termed $Pam_3Cys$. It has been shown that lipidation of OspA is necessary for immunogenicity, since OspA lipoprotein with an N-terminal $Pam_3Cys$ moiety stimulated a strong antibody response, while ospA lacking the attached lipid did not induce any detectable antibodies [Erdile et al., Infect. Immun., (1993), 61:81–90].

Published international patent application WO 91/09870 (Mikrogen Molekularbiologische Entwicklungs-GmbH) describes the DNA sequence of the ospC gene of *B. burgdorferi* strain Pko and the OspC (termed pC in this reference) protein encoded thereby of 22 kDa molecular weight. This sequence reveals that OspC is a lipoprotein that employs a signal sequence similar to that used for OspA. Based on the findings regarding OspA, one might expect that lipidation of recombinant OspC would be useful to enhance its immunogenicity; but, as discussed below, the applicants experienced difficulties in obtaining detectable expression of recombinant OspC.

U.S. Pat. No. 4,624,926 to Inouye relates to plasmid cloning vectors, including a DNA sequence coding for a desired polypeptide linked with one or more functional fragments derived from an outer membrane lipoprotein gene of a gram negative bacterium. The polypeptide expressed by the transformed *E. coli* host cells comprises the signal peptide of the lipoprotein, followed by the first eight amino acid residues of the lipoprotein, which in turn are followed by the amino acid sequence of the desired protein. The signal peptide may then be translocated naturally across the cytoplasmic membrane and the first eight amino acids of the lipoprotein may then be processed further and inserted into the outer membrane of the cell in a manner analogous to the normal insertion of the lipoprotein into the outer membrane. Immunogenicity of the expressed proteins was not demonstrated. Moreover, Inouye was not at all concerned with recombinant lipidation, particularly to enhance immunogenicity.

Published international patent application WO91/09952 describes plasmids for expressing lipidated proteins. Such plasmids involve a DNA sequence encloding a lipoprotein signal peptide linked to the codons for one of the β-turn tetrapeptides QANY or IEGR, which in turn is linked to the DNA sequence encoding the desired protein. Again, immunogenicity of the expressed proteins was not demonstrated.

*Streptoccus pneumoniae* causes more fatal infections world-wide than almost any other pathogen. In the U.S.A., deaths caused by *S. pneumoniae* rival in numbers those caused by AIDS. Most fatal pneumoccal infections in the U.S.A. occur in individuals over 65 years of age, in whom *S. pneumoniae* is the most common cause of community-acquired pneumonia. In the developed world, most pneumococcal deaths occur in the elderly, or in immunodeficient patents including those with sickle cell disease. In the less-developed areas of the world, pneumococcal infection is one of the largest causes of death among children less than 5 years of age. The increase in the frequency of multiple antibiotic resistance among pneumococci and the prohibitive cost of drug treatment in poor countries make the present prospect for control of pneumococcal disease problematical.

The reservoir of pneumococci that infect man is maintained primarily via nasopharyngeal human carriage. Humans acquire pneumococci first through aerosols or by direct contact. Pneumococci first colonize the upper airways and can remain in nasal mucosa for weeks or months. As many as 50% or more of young children and the elderly are colonized. In most cases, this colonization results in no apparent infection. In some individuals, however, the organism carried in the nasopharynx can give rise to symptomatic sinusitis of middle ear infection. If pneumococci are aspirated into the lung, especially with food particles or mucus, they can cause pneumonia. Infections at these sites generally shed some pneumococci into the blood where they can lead to sepsis, especially if they continue to be shed in large numbers from the original focus of infection. Pneumococci in the blood can reach the brain where they can cause menigitis. Although pneumococcal meningitis is less common than other infections caused by these bacteria, it is particularly devastating; some 10% of patients die and greater than 50% of the remainder have life-long neurological sequelae.

In elderly adults, the present 23-valent capsular polysaccharide vaccine is about 60% effective against invasive pneumococcal disease with strains of the capsular types included in the vaccine. The 23-valent vaccine is not effective in children less than 2 years of age because of their inability to make adequate responses to most polysaccharides. Improved vaccines that can protect children and adults against invasive infections with pneumococci would help reduce some of the most deleterious aspects of this disease.

The *S. pneumoniae* cell surface protein PspA has been demonstrated to be a virulence factor and a protective antigen. In published international patent application WO 92/14488, there are described the DNA sequences for the pspA gene from *S. pneumoniae* Rx1, the production of a truncated form of PspA by genetic engineering, and the demonstration that such truncated form of PspA confers protection in mice to challenge with live pneumococci.

In an effort to develop a vaccine or immunogenic composition based on PspA, PspA has been recombinantly expressed in *E. coli*. It has been found that in order to efficiently express PspA, it is useful to truncate the mature PspA molecule of the Rx1 strain from its normal length of 589 amino acids to that of 314 amino acids comprising amino acids 1 to 314. This region of the PspA molecule contains most, if not all, of the protective epitopes of PspA. However, immunogenicity and protection studies in mice have demonstrated that the truncated recombinant form of PspA is not immunogenic in naive mice. Thus, it would be useful to improve the immunogenicity of recombinant PspA and fragments thereof.

Many bacterial and viral pathogens, such as *S. pneumoniae* and *Helicobacter pylori*, and HIV, herpes and papilloma viruses gain entry through mucosal surfaces. The principal determinant of specific immunity at mucosal surfaces is secretory IgA (S-IgA) which is physiologically and functionally separate from the components of the circulatory immune system. Mucosal S-IgA responses are predominantly generated by the common mucosal immune system (CMIS) [Mestecky, J. Clin. Immunol. (1987), 7:265–276], in which immunogens are taken up by specialized lymphoepithelial structures collectively referred to as mucosa-associated lymphoid tissue (MALT). The term common mucosal immune system referes to the fact that immunization at any mucosal site can elicit an immune response at all other mucosal sites. Thus, immunization in the gut can elicit mucosal immunity in the upper airways and vice versa. Further, it is important to note that oral immunization can induce an antigen-specific IgG response in the systemic compartment in addition to mucosal IgA antibodies [McGhee, J. R. et al., (1993), Infect. Agents and Disease 2:55–73].

Most soluble and non-replicating antigens are poor mucosal immunogens, especially by the peroral route, probably because they are degraded by digestive enzymes and have little or no tropism for the gut associated lymphoid tissue (GALT). Thus, a method for producing effective mucosal immunogens, and vaccines and immunogenic compositins containing them, would be desirable.

Of particular interest is *H. pylori*, the spiral bacterium which selectively colonizes human gastric mucin-secreting cells and is the causative agent in most cases of nonerosive gastritis in humans. Recent research indicates that *H. pylori*, which has a high urease activity, is responsible for most peptic ulcers as well as many gastric cancers. Many studies have suggested that urease, a complex of the products of the ureA and ureB genes, may be a protective antigen, However, until now it has not been known how to produce a sufficient mucosal immune response to urease.

Antigens, such as OspC, PspA, UreA, UreB or immunogenic fragments thereof, stimulate an immune response when administered to a host. Such antigens, especially when recombinantly produced, may elicit a stronger response when administered in conjunction with an adjuvant. Currently, alum is the only adjuvant licensed for human use, although hundreds of experimental adjuvants such as cholera toxin B are being tested. However, these adjuvants have deficiencies. For instance, while cholera toxin B is not toxic in the sense of causing cholera, there is general unease about administering a toxin associated with a disease as harmful as cholera, especially if there is even the most remote chance of minor impurity.

Thus, it would be desirable to enhance the immunogenicity of antigens, by methods other than the use of an adjuvant, especially in monovalent preparations; and, in multivalent preparations, to have the ability to employ such a means for enhanced immunogenicity with an adjuvant, so as to obtain an even greater immunological response.

As to expression of recombinant proteins, it is expected that the skilled artisan is familiar with the various vector systems available for such expression, e.g., bacteria such as *E. coli* and the like.

It is believed that heretofore the art has not taught or suggested expression of a recombinant lipoprotein wherein the lipidation thereof is from expression of a first nucleic acid sequence, the protein thereof is from expression of a second nucleic acid sequence, the first and second sequences, which do not naturally occur together, being contiguous, especially such a lipoprotein wherein the first sequence a Borrelia lipoprotein leader sequence, preferably an OspA leader sequence, and even more preferably wherein the first sequence encodes an OspA leader sequence and the second sequence encodes OspC, PspA, UreA, UreB, or an immunogenic fragment thereof; or genes containing such sequences; or vectors containing such sequences; or methods for such expression; or such recombinant lipoproteins; or compositions containing such recombinant lipoproteins; or methods for using such compositions; or methods for enhancing the immunogenicity of a protein by lipidation from a nucleic acid sequence not naturally occurring with the nucleic acid sequence encoding the protein portion of the lipoprotein.

OBJECTS AND SUMMARY OF THE INVENTION

It is an object of the invention to provide a recombinant lipoprotein wherein the lipidation thereof is from expression of a first nucleic acid sequence and the protein portion thereof is from expression of a second nucleic acid sequence and the first and second sequences do not naturally occur together; especially such a lipoprotein wherein the first sequence encodes a Borrelia lipoprotein leader sequence, preferably an ospA leader sequence, and more preferably wherein the second sequence encodes a protein portion comprising OspC, PspA, UreA, UreB, or an immunogenic fragment thereof.

It is another object of the invention to provide expression of genes and/or sequences encoding such a recombinant lipoprotein, vectors therefor and methods for effecting such expression.

It is a further object of the invention to provide immunogenic compositions, including vaccines, containing the recombinant lipoproteins and/or vectors for expression thereof.

It has surprisingly been found that an immunogenic recombinant lipidated protein, preferably OspC or a portion thereof, can be expressed from a vector system, preferably *E. coli*, without the toxicity to the vector system evident when the native lipoprotein signal sequence encoding region is present. This result has been achieved by replacing the nucleotide sequence encoding the native leader or signal sequence of a lipoprotein with the nucleotide sequence encoding a leader or signal of another lipoprotein, preferably of a Borrelia lipoprotein, and more preferably the OspA leader or signal sequence. Proteins not naturally lipidated, such as PspA, UreA, and UreB, may be expressed as recombinant lipidated proteins as well, by fusing lipoprotein signal sequence to the first amino acid of the desired protein. These recombinant lipidated proteins have been shown to elicit an immune response, including a mucosal immune response.

It is surprising that fusion of DNA encoding a lipoprotein leader sequence directly to the DNA encoding a protein, without any intervening nucleotide sequences, can lead to expression of an immunogenic recombinant lipoprotein in significant quantities without the toxicity evident with the native leader sequence, because previous attempts to express recombinant lipidated proteins have been unsuccessful. For example, Fuchs et al. report that recombinantly formed OspC (referred to as pC in this reference) with its native leader protein was only weakly expressed in *E. coli* [Mol. Microbiology (1992) 6(4):503–509]. Applicants, in addition to Fuchs, attempted to obtain lipidated recombinant OspC by expression of the OspC-encoding sequence in *E. coli* using the pET vector system described in the aforementioned WO 92/14488 for the expression of OspA and using the pDS12 plasmid systems described. However, OspC was barely detectable by immunoblotting of cell extracts using these systems to express OspC.

Further, as discussed supra, it was believed that an additional nucleotide sequence, preferably one encoding a peptide sequence forming a β-turn, was necessary for expression of recombinant lipoproteins, and the immunogenicity of recombinant lipoproteins previously expressed had not been demonstrated.

The procedure of the present invention, therefore, enables large quantities of pure recombinant, immunogenic lipidated proteins, e.g., OspC, PspA, UreA, UreB and portions thereof, to be obtained, which has not heretofore been possible. The recombinantly-formed lipidated proteins provided herein are significantly more immunogenic than a non-lipidated recombinant analog.

The present invention, it is believed, represents the first instance of effecting expression of a heterologous lipidated protein using a non-native, preferably Borrelia and more preferably the OspA leader sequence. The invention, therefore, includes the use of non-native, preferably Borrelia and more preferably the OspA leader sequence to express proteins heterologous to the leader sequence.

Accordingly, in one embodiment, the present invention provides an isolated hybrid nucleic acid molecule, preferably DNA, comprising a first nucleic acid sequence encoding the signal sequence preferably of an OspA protein of a Borrelia species, coupled in translational open reading frame relationship with a second nucleic acid sequence encoding a mature protein heterologous to the signal sequence, preferably to OspC or PspA. More preferably, the first and second sequences are contiguous when the mature protein is naturally lipidated, and separated by one codon coding for one amino acid, preferably cysteine, when the mature protein is not naturally lipidated.

The mature protein encoded by the second nucleic acid sequence generally is a lipoprotein, preferably an antigenic lipoprotein,an more preferably is the mature OspC lipoprotein of a Borrelia species, preferably a strain of *B. burgdorferi*, more preferably a strain of *B. burgdorferi* selected from the OspC sub-type families. In another preferred embodiment, the mature protein is the mature PspA protein, or an immunogenic fragment thereof, of a strain of *S. pneumoniae*. In yet another preferred embodiment, the mature protein is UreA or UreB protein of a strain of *H. pylori*. Similarly, the signal sequence of the OspA protein of a Borrelia strain encoded by the first nucleic acid sequence preferably is that of a strain of *B. burgdorferi*, more preferably a strain of *B. burgdorferi* selected from the B31, ACA1 and Ip90 families of strains.

The hybrid gene provided herein may be assembled into an expression vector, preferably under the control of a suitable promoter for expression of the mature lipoprotein, in accordance with a further aspect of the invention, which, in a suitable host organism, such as *E. coli*, causes initial translation of a chimeric molecule comprising the leader sequence and the desired heterologous protein in lipidated form, followed by cleavage of the chimeric molecule by signal peptidase II and attachment of lipid moieties to the new terminus of the protein, whereby the mature lipoprotein is expressed in the host organism.

The present invention provides, for the first time, a hybrid nucleic acid molecule which permits the production of recombinant lipidated protein, e.g., recombinant lipidated OspC of a Borrelia species, recombinant lipidated PspA of a strain of *S. pneumoniae* or recombinant lipidated UreA or UreB of a strain of *H. pylori*, to be obtained. Accordingly, in a further aspect of this invention, there is provided a hybrid nucleic acid molecule, comprising a first nucleic acid sequence encoding a lipoprotein, preferably an OspC lipoprotein of a Borrelia species, more preferably a strain of *B. burgdorferi*, still more preferably a strain of *B. burgdorferi* selected from the OspC sub-type families; or encoding a PspA lipoprotein of a strain of *S. pneumoniae* or immunogenic fragment thereof; or encoding a UreA or UreB lipoprotein of a strain of *H. pylori*; and a second nucleic acid sequence encoding a signal sequence of an expressed protein heterologous to the protein encoded by the first nucleic acid sequence and coupled in translational open reading frame relationship with said first nucleic acid sequence, preferably encoding the signal sequence of an OspA protein of a Borrelia species.

As described above, the hybrid gene can be assembled into an expression vector under the control of a suitable promoter for expression of the lipoprotein, which, in a suitable host organism, such as *E. coli*, causes expression of the lipoprotein from the host organism.

It has also surprisingly been found that enhanced immunogenicity can be obtained by a recombinant lipoprotein when the lipoprotein is expressed by a hybrid or chimeric gene comprising a first nucleic acid sequence encoding a leader or signal sequence and a second nucleic acid sequence encoding the protein portion of the lipoprotein, wherein the first and second sequences do not naturally occur together.

Accordingly, the present invention also provides a recombinant lipoprotein expressed by a hybrid or chimeric gene comprising a first nucleic acid sequence encoding a leader or signal sequence contiguous with a second nucleic acid sequence encoding a protein portion of the lipoprotein, and the first and second sequences do not naturally occur together. The first and second sequences are preferably coupled in a translational open reading frame relationship. The first sequence can encode a leader sequence of a Borrelia lipoprotein, preferably the leader sequence of OspA; and the second sequence can encode a protein comprising an antigen, preferably OspC, PspA, UreA, UreB or an immunogenic fragment thereof. The first and second sequences can be present in a gene; and the gene and/or the first and second sequences can be in a suitable vector for expression.

The vector can be a nucleic acid in the form of, e.g., plasmids, bacteriophages and integrated DNA, in a bacteria, most preferably one used for expression, e.g. *E. coli, Bacillus subtilis*, Salmonella, Staphylocoocus, Streptococcus, etc., or one used as a live vector, e.g. Lactobacillus, Mycobacterium, Salmonella, Streptococcus, etc. When an expression host is used the recombinant lipoprotein can be obtained by harvesting product expressed in vitro; e.g., by isolating the recombinant lipoprotein from a bacterial extract. The gene can preferably be under the control of and therefore operably linked to a suitable promoter; and the promoter can either be endogenous to the vector, or be inserted into the vector with the gene.

The invention further provides vectors containing the nucleic acid encoding the recombinant lipoprotein and methods for obtaining the recombinant lipoproteins and methods for preparing the vector.

As mentioned, the recombinant lipoprotein can have enhanced immunogenicity. Thus, additional embodiments of the invention provide immunogenic or vaccine compositions for inducing an immunological response, comprising the isolated recombinant lipoprotein, or a suitable vector for in vivo expression thereof, or both, and a suitable carrier, as well as to methods for eliciting an immunological or protective response comprising administering to a host the isolated recombinant lipoprotein, the vector expressing the recombinant lipoprotein, or a composition containing the recombinant lipoprotein or vector, in an amount sufficient to elicit the response.

Documents cited in this disclosure, including the above-referenced applications, provide typical additional ingredients for such compositions, such that undue experimentation is not required by the skilled artisan to formulate a composition from this disclosure. Such compositions should preferably contain a quantity of the recombinant lipoprotein or vector expressing such sufficient to elicit a suitable response. Such a quantity of recombinant lipoproprotein or vector can be based upon known amounts of antigens administered. For instance, if there is a known amount for administration of an antigen corresponding to the second sequence expressed for the inventive recombinant lipoprotein, the quantity of recombinant lipoprotein can be scaled to about that known amount, and the amount of vector can be such as to produce a sufficient number of colony forming units (cfu) so as to result in in vivo expression of the recombinant lipoprotein in about that known amount. Likewise, the quantity of recombinant lipoprotein can be based upon amounts of antigen administered to animals in the examples below and in the documents cited herein, without undue experimentation.

The present invention also includes, in other aspects, processes for the production of a recombinant lipoprotein, by assembly of an expression vector, expression of the lipoprotein from a host organism containing the expression vector, and optionally isolating and/or purifying the expressed lipoprotein. The isolating/purifying can be so as to obtain recombinant lipoprotein free from impurities such as lipopolysaccharides and other bacterial proteins. The present invention further includes immunogenic compositions, such as vaccines, containing the recombinant lipoprotein as well as methods for inducing an immunological response.

BRIEF DESCRIPTION OF DRAWINGS

In the following detailed description, reference is made to the accompanying drawings, wherein:

FIG. 4 is a schematic representation of the procedure employed for the isolation and purification of non-lipidated OspC for comparative purposes;

FIG. 12 is a schematic representation of the procedure employed for the isolation and purification of non-lipidated PspA for comparative purposes;

FIG. 13 shows an SDS-PAGE analysis of lipidated PspA produced herein at various states of the expression and host cell fractionation procedure illustrated schematically in FIG. 11;

DETAILED DESCRIPTION OF INVENTION

As noted above, the present invention is concerned with the use of a nucleic acid sequence encoding the OspA signal sequence to express lipidated proteins heterologous to OspA protein, preferably an OspC protein of a Borrelia species, a PspA protein or portion thereof of a strain of *S. pneumoniae*, or a UreA or UreB protein of a strain of *H. pylori*, and to the use of a nucleic acid sequence encoding the signal sequence of a protein heterologous to the protein to be expressed, to express the lipidated OspC protein of a Borrelia species or the lipidated PspA protein of a strain of *S. pneumoniae*.

The leader amino acid sequence and encoding DNA sequence for the ACA strain of *B. burgdorferi* are as follows:
M K K Y L L G I G L I L A L I A C (SEQ ID NO: 1)
ATG AAA AAA TAT TTA TTG GGA ATA GGT CTA ATA TTA GCC TTA ATA GCA TGC (SEQ ID NO: 2)
The corresponding leader amino acid sequences and encoding DNA sequences for the OspA of other strains of *B. burgdorferi* are known in the art and may be employed in the present invention from this disclosure, without any undue experimentation.

A hybrid gene molecule is assembled comprising the OspA leader encoding sequence and the gene encoding the heterologous protein to be expressed, preferably the ospC or pspA gene, arranged in translational reading-frame relationship with the ospA gene fragment.

For production of the lipidated protein, the appropriate hybrid gene molecule can be incorporated into a suitable expression vector and the resulting plasmid incorporated into an expression strain of *E. coli* or other suitable host organism. The vector can also be a bacteriophage or integrated DNA.

Figure 3:
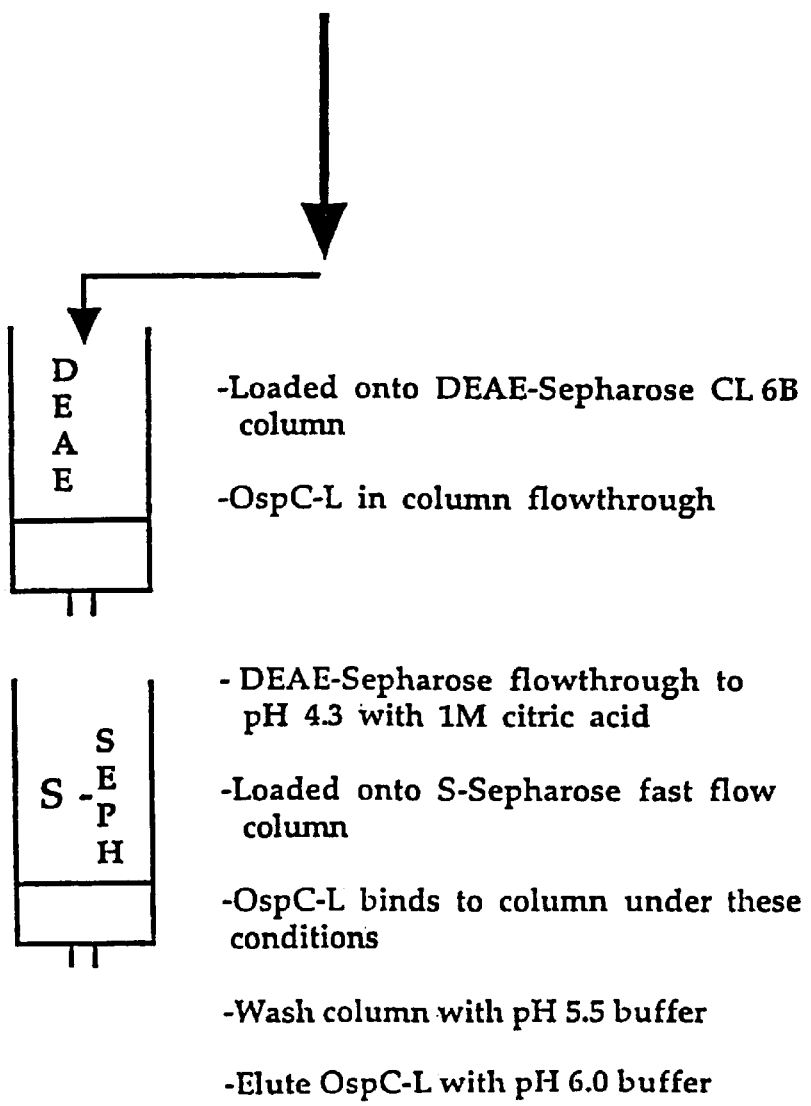
FIG. 3 is a schematic representation of the procedure employed for the isolation and purification of lipidated OspC.

The lipidated protein is expressed by the cells during growth of the host organism. The lipidated protein may be recovered from the host organism in purified form by any convenient procedure which separates the lipidated protein in undenatured form. One schematic of a procedure in accordance with this aspect of the invention is shown in FIG. 3.

Following cell growth and induction of protein, the cells are subjected to freeze-thaw lysis and DNase I treatment. The lysate is treated with a detergent which is selective for solubilization of the recombinant lipidated protein, in preference to the other bacterial proteins in the lysate. While the present invention preferably utilizes polyethylene glycol tert-octylphenyl ether having the formula t-Oct-$C_6H_4$—$(OCH_2CH_2)_xOH$ wherein x=7–8 as the detergent (commercially available as, and hereinafter referred to as, TRITON™ X-114), other materials may be used exhibiting a similar selective solubility for the lipidation protein as well as the phase separation property under mild conditions, as discussed below.

Following addition of the TRITON™ X-114, the mixture is warmed to a mild temperature elevation of preferably about 35° C. to 40° C., at which time the solution becomes cloudy as phase separation occurs. The purification procedure for such phase separation should occur under conditions to avoid any substantial denaturing or any other substantial impairment of the immunological properties of the recombinant lipoprotein.

Centrifugation of the cloudy mixture results in separation of the mixture into three phases, namely a detergent phase containing about 50% or more of the recombinant lipidate protein and a small amount (approximately 5 wt %) of other proteins, an aqueous phase containing the balance of the other proteins, and a solid pellet of cell residue. The detergent phase is separated from the aqueous phase and the solid pellet for further processing.

Final purification of the protein preferably is effected by processing of the detergent phase to provide a recombinant lipidated protein having a purity of at least about 80 wt %, and which is substantially free from other contaminants such as bacterial proteins, and lipopolysaccharides (LPS), and which has endotoxin levels compatible with human administration.

Such purification is conveniently effected by column chromatography. Such chromatographic purification may include a first chromatographic purification using a first chromatographic column having the pH, ionic strength and hydrophobicity to bind bacterial proteins, but not the recombinant lipidated protein.

Such first chromatographic purification may be effected by loading the detergent phase onto the first chromatographic column and the flow-through, which contains the purified lipidated protein, is collected. The bound fraction contains substantially all the bacterial protein impurities from the detergent phase. The chromatography medium used for such first purification operation may be a DEAE-Sephacel or DEAE-Sepharose column.

The flow-through from the first chromatographic purification operation may be subjected to further purification on a second chromatographic column. The flow-through is loaded onto the column having the pH, ionic strength and hydrophobicity which will selectively bind the recombinant lipidated protein to the second chromatographic column, while bacterial contaminants and LPS pass through the column. The chromatography medium for the second chromatographic column may be S-Sepharose.

Preferably the recombinant lipoprotein is purified to 80% purity or to greater than 80% purity, e.g., 85–90% or even 90–95% or greater than 95% purity. The lipidated proteinaceous material can then be formulated into immunogenic compositions, preferably vaccines.

The vaccine or immunogenic composition elicits an immune response in a host subject which produces an immunological response, such as antibodies which may be opsonizing or bactericidal. Should a subject immunized with a recombinant lipoprotein of the invention then be challenged, such immunological response can inactivate the challenge organism. Furthermore, opsonizing or bactericidal antibodies may also provide protection by alternative mechanisms.

Immunogenic compositions including vaccines can be prepared as injectables, as liquid solutions or emulsions, or as formulating for oral, nasal or other orifice administration e.g., vaginal, rectal, etc. Oral formulations can be liquid solutions, emulsions and the like, e.g., elixers, or solid preparations, e.g., tablets, caplets, capsules, pills, liquid-filled-capsules, gelatin and the like. Nasal preparations can be liquid and can be administered via aerosol, squeeze spray or pump spray dispensers. Documents cited herein provide exemplary formulation types and ingredients therefor, including the applications cited above.

The immunogens can be mixed with pharmaceutically acceptable excipients which are compatible with the immunogens. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. The immunogenic preparations and vaccines are administered in a manner compatible with the dosage formulation, and in such amount as will be therapeutically effective, immunogenic or protective. The quantity to be administered depends on the Subject to be treated, including, for example, the capacity of the immune system of the individual to synthesize antibodies, and, if needed, to produce a cell-mediated immune response. Precise amounts of active ingredient required to be administered depend on the judgment of the practitioner, taking into account such factors as the age, weight, sex, condition of the host or patient to whom there is to be administration. However, suitable dosage ranges are readily determinable by one skilled in the art and may be of the order of micrograms of the immunogens. Suitable regimes for initial administration and booster doses are also variable, but may include an initial administration followed by subsequent administrations. The dosage may also depend on the route of administration and will vary according to the size of the host.

The concentration of the immunogens in an immunogenic composition according to the invention is in general about 1 to about 95%. A vaccine or immunogenic composition which contains antigenic material of only one pathogen is a monovalent vaccine. Vaccines or immunogenic ocmpositions which are multivalent or which contain antigenic material of several pathogens (also known as combined vaccines or combined imunogenic compositions) also belong to the present invention. Such combined vaccines or immunogenic compositions contain, for example, material from various pathogens or from various strains of the same pathogen, or from combinations of various pathogens.

Immunostimulatory agents or adjuvants have been used for many years to improve the host immune responses to, for example, vaccines or immunogenic compositions. Intrinsic adjuvants, such as lipopolysaccharides, normally are the components of the killed or attenuated bacteria used as vaccines or immunogenic compositions. Extrinsic adjuvants are immunomodulators which are typically non-covalently linked to antigens and are formulated to enhance the host immune responses. Some of these adjuvants are toxic, however, and can cause undesirable side-effects, making them unsuitable for use in humans and many animals. Indeed, only alum is routinely used as an adjuvant in human and veterinary vaccines.

In view of the difficulties associated with the use of adjuvants, it is thus an advantage of the present invention that the recombinant lipidated proteins are the most immunogenic forms, and are capable of eliciting immune responses both without any adjuvant and with alum.

The following examples illustrate but do not limit the scope of the invention disclosed in this specification.

EXAMPLES

Example 1

Construction of a Vector Containing a Gene Encoding the OspA Leader Sequence

Figure 1:
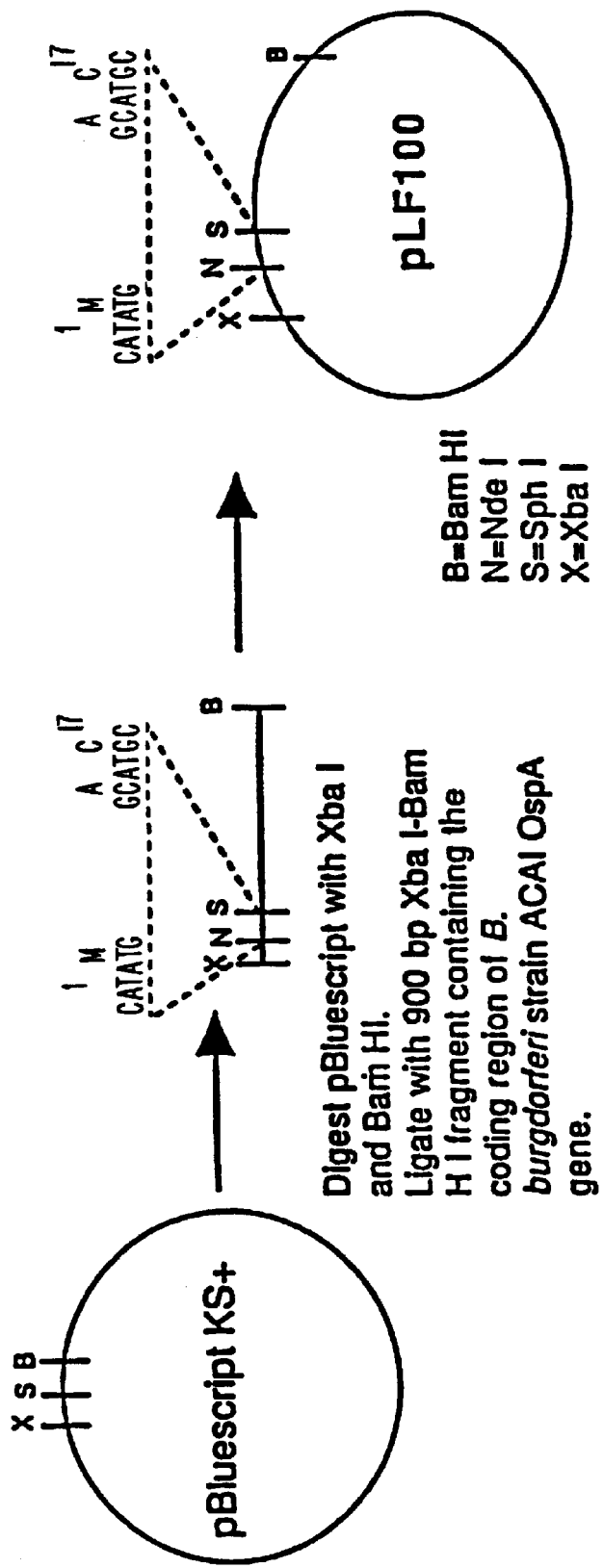
FIG. 1 is a schematic representation of a procedure for assembling plasmid pLF100.

Plasmid pBluescript KS+ (Stratagene) was digested with XbaI and BamHI and ligated with a 900 bp XbaI-BamHI DNA fragment containing the complete coding region of *B. burgdorferi* strain ACA1 ospA gene, to form a lipoprotein fusion vector pLF100. This procedure is shown schematically in FIG. 1.

The vector pLF100, has been deposited with the American Type Culture Collection 10801 University Blvd., Mansas, Va. 20110-2209 on Feb. 2, 1995 under Accession No. 69750. This deposit was made under the terms of the Budapest Treaty.

Example 2

Construction of a Expression Vector Containing a Hybrid ospA-ospC Gene

Specifically designed oligonucleotide primers were used in a polymerase chain reaction (PCR) to amplify the portion of the ospC gene downstream from the cysteine-encoding codon terminating the signal-peptide recognition-encoding sequence to the C-terminal end of the coding region from the Pko and B31 strains of *B. burgdorferi*.

The 5'-end primer had the nucleotide sequences respectively for the Pko and B31 strains:
5'-GGC GCG CAT GCA ATA ATT CAG GGA AAG G-3' (Pko) (SEQ ID NO: 3)
5'-GGC GCG CAT GCA ATA ATT CAG GGA AAG A-3' (B31) (SEQ ID NO: 4)
while the 3'-end primer had the nucleotide sequence:
5'-CGC GGA TCC TTA AGG TTT TTT TGG-3' (B31 & Pko) (SEQ ID NO: 5)

The PCR amplification was effected in a DNA Thermal Cycler (Perkins-Elmer Cetus) for 25 cycles with denaturation for 30 secs at 94° C., annealing at 37° C. for 1 minute and extension at 72° C. for 1 minute. A final extension was effected at 72° C. for 5 minutes at the completion of the cycles. The product was purified using a Gene Clean II kit (B10 101) and the purified material was digested with SphI and BamHI. This procedure introduced a silent mutation in the Pko ospC gene which changes the codon for amino acid 60 of the mature protein from ATT to ATA.

The materials produced for the Pko and B31 *B. burgdorferi* strains were handled identically from this point on and hence only the further handling of the Pko strain OspC material is described.

Figure 2:
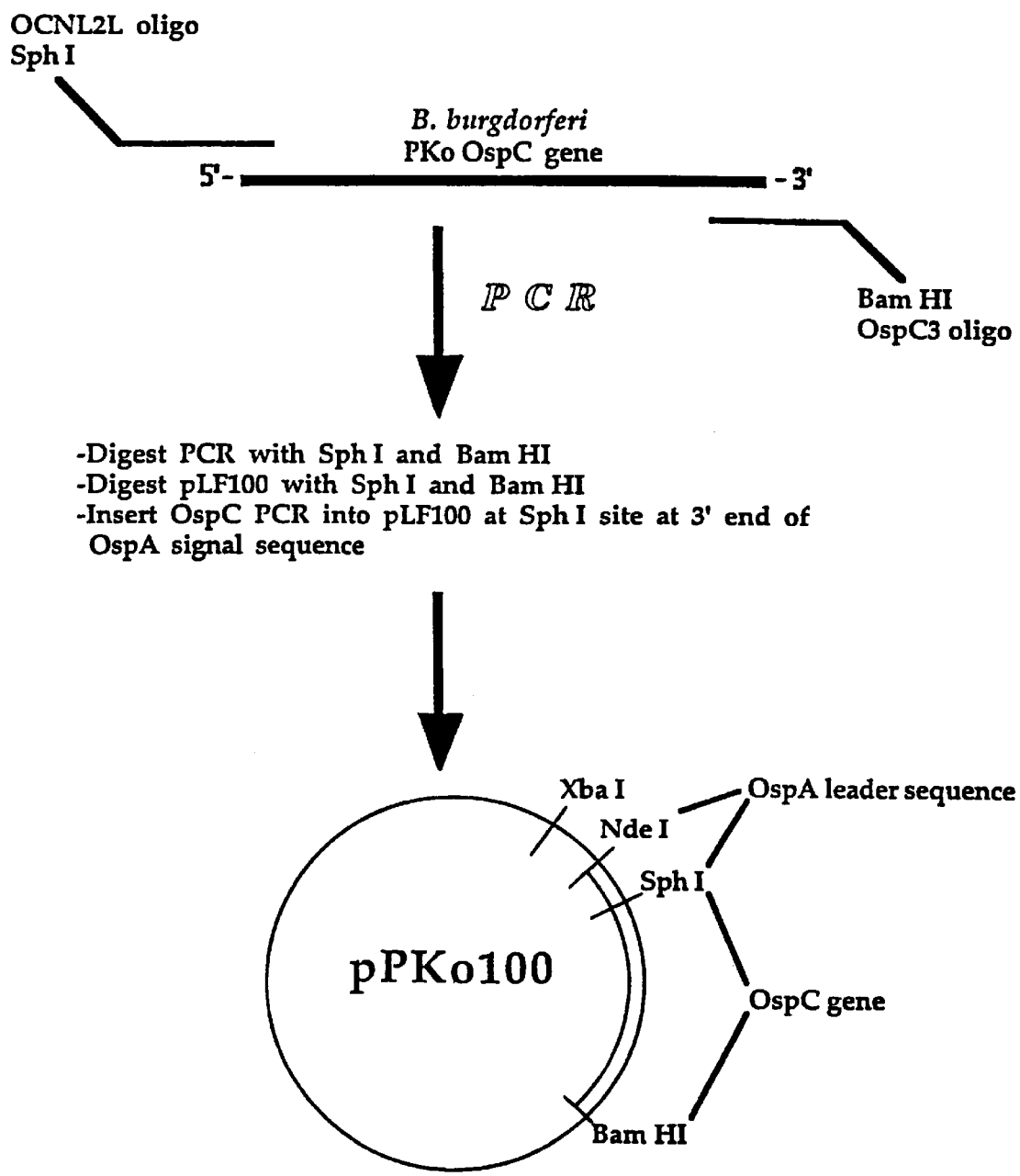
FIG. 2 is a schematic representation of a procedure for assembling plasmid vectors pPko9a (strain Pko) and pB319a (strain B31)

The plasmid pLF100 (Example 1) was digested with SphI and BamHI and the amplified PKo sequence was ligated into the plasmid to form plasmid pPko 100 (pB31 100 for the B31 strain) containing a hybrid ospA/ospC gene. The hybrid gene was excised from plasmid pPko 100 by digestion with NdeI and BamHI and cloned into the NdeI and BamHI sites of the plasmid vector pET9 to place the ospA/ospC hybrid gene under control of a T7 promoter and efficient translation initiation signals from bacteriophage T7, as seen in FIG. 2. The resulting plasmid is designated pPko9a (pB319a for the B31 strain).

Example 3

Expression and Purification of Lipidated OspC

Plasmid pPko9a, prepared as described in Example 2, was used to transform *E. coli* strains BL21(DE3)(pLysS) and HMS174(DE3)(pLysS). The transformed *E. coli* was inoculated in to LB media with 30 μg/ml kanamycin sulfate and 25 μg/ml of chloramphenicol at a rate of 12 ml of culture for every liter prepped. The culture was grown overnight in a flask shaker at 37° C.

The next morning, 10 ml of overnight culture medium was transferred to 1 L of LB media containing 30 μg/ml of kanamycin sulfate and the culture was grown in a flask shaker at about 37° C. to a level of $OD_{600}$=0.6–1.0 (although growth up to $OD_{600}$=1.5 can be effected), in approximately 3–5 hours.

Figure 5:
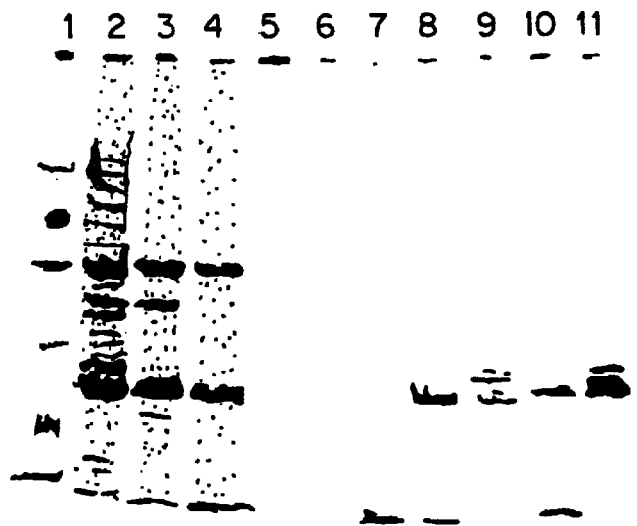
FIG. 5 shows an SDS-PAGE analysis of lipidated OspC produced herein at various stages of the purification procedure illustrated schematically in FIG. 3.

To the culture medium was added isopropylthiogalactoside (IPTG) to a final concentration of 0.5 mM and the culture medium was grown for a further two hours at about 30° C. The cultures were harvested and samples analyzed on Coomassie stained SDS-PAGE gels (FIG. 5). The culture medium was cooled to about 4° C. and centrifuged at 10,000×G for 10 minutes. The supernatant was discarded while the cell pellet was collected. Purified lipidated OspC was recovered from the pellet by effecting the procedure shown schematically in FIG. 3 and described below.

The cell pellet first was resuspended in 1/10 the volume of PBS. The cell suspension was frozen and stored at −20°

C. or below, if desired. Following freezing of the cell suspension, the cells were thawed to room temperature (about 20° to 25° C.) which causes the cells to lyse. DNase I was added to the thawed material to a concentration of 1 µg/ml and the mixture was incubated for 30 minutes at room temperature, which resulted in a decrease in the viscosity of the material.

The incubated material was chilled on ice to a temperature below 10° C. and TRITON™ X-114 was added as a 10 wt % stock solution, to a final concentration of 0.3 to 1 wt %. The mixture was kept on ice for 20 minutes. The chilled mixture next was heated to about 37° C. and held at that temperature for 10 minutes.

The solution turned very cloudy as phase separation occurred. The cloudy mixture then was centrifuged at about 20° C. for 10 minutes at 12,000×G, which caused separation of the mixture into a lower detergent phase, an upper clear aqueous phase and a solid pellet. Analysis of the phases fractionated by SDS-PAGE (FIG. 5) revealed that the OspC partitioned into the detergent phase, showing that it is in lipidated form. The detergent phase was separated from the other two phases and cooled to 4° C., without disturbing the pellet.

Buffer A, namely 50 mM Tris pH 7.5, 2 mM EDTA and 10 mM NaCl and 0.3% polyethylene glycol tert-octylphenyl ether having the formula t-Oct-$C_6H_4$—$(OCH_2CH_2)_xOH$ wherein x=9–10 as the detergent (commercially available as, and hereinafter referred to as, TRITON™ X-100), was added to the cooled detergent phase to reconstitute back to ⅓ the original volume. The resulting solution may be frozen and stored for later processing as described below or may be immediately subjected to such processing.

A DEAE-Sepharose CL-6B column was prepared in a volume of 1 ml/10 ml of detergent phase and was washed with 2 volumes of Buffer C, namely 50 mM Tris pH 7.5, 2 mM EDTA, 1 M NaCl, 0.3 wt % TRITON™ X-100, and then with 4 volumes of Buffer B, namely 50 mM Tris pH 7.5, 2 mM EDTA, 0.3 wt % TRITON™ X-100.

The detergent phase then was loaded onto the column and the flow-through containing the OspC, was collected. The column was washed with 2 volumes of Buffer B and the flow-through again was collected. The combined flow-through was an aqueous solution of purified OspC, which may be frozen for storage.

The column may be freed from bacterial proteins for reuse by eluting with 4 volumes of Buffer C.

Further and final purification of the flow-through from the DEAE-Sepharose column was effected by chromatography on S-Sepharose Fast Flow. The flow-through from the DEAE-Sepharose column first was acidified to pH 4.3 by the addition of 1 M citric acid and the acidified material was loaded onto the S-Sepharose column. The S-Sepharose Fast Flow column had been washed with 3 column volumes of Buffer A and then with 5 column volumes of Buffer A made up to pH 4.3. The OspC binds to the column. The loaded column was washed with 4 column volumes of pH 4.3 Buffer A followed by 4 column volumes of pH 5.5 Buffer A.

Highly-purified OspC was eluted from the column using Buffer A, adjusted to pH 6.0 with 1N HCl. A schematic of the purification process described in this Example is shown in FIG. 3.

The aqueous solution of highly purified lipidated OspC obtained by the chromatography procedures was analyzed by Coomassie stained gels (FIG. 5), and confirmed to be OspC in highly purified form by immunoblot analysis using rabbit anti-OspC polyclonal antiserum. The purity of the product was estimated to be greater than 80%.

By this procedure, about 2 to 4 mg of pure OspC was recovered from a 1 liter culture of the BL21 host and about 1 to 2 mg of pure OspC was recovered from a 1 liter culture of the HMS 174 host.

Example 4

Expression and Purification of Non-lipidated OspC

*E. coli* JM 109 transformants containing plasmid vector containing chromosomal gene fragment encoding non-lipidated OspC were prepared and grown as described in WO 91/09870. The cultures were harvested, the culture medium centrifuged at 10,000×G for 10 minutes at 4° C., the supernatant discarded and the pellet collected.

The cell pellet was first resuspended in lysis buffer A, namely 50 nM Tris-HCl pH 8.0, 2 mM EDTA, 0.1 mM DTT, 5% glycerol and 0.4 mg/ml lysozyme, and the suspension stirred for 20 minutes at room temperature. TRITON™ X-100 then was added to the cell suspension to a concentration of 1 wt %, DNase I was added to a concentration of 1 µg/ml, and the suspension stirred at room temperature for a further 20 minutes to effect cell lysis. Sodium chloride next was added to the cell suspension to a concentration of 1M and the suspension again stirred at 4° C. for a further 20 minutes. The suspension then was centrifuged at 20,000×G for 30 minutes, the resultant supernatant separated from the pellet and the pellet was discarded.

The separated supernatant was dialyzed against a buffer comprising 50 mM Tris pH 8, 2 mM EDTA. The supernatant next was loaded onto a DEAE-Sepharose CL-6B column and the non-lipidated OspC was collected in the column flow-through. The flow-through was dialyzed against a 0.1 M phosphate buffer, pH 6.0.

The dialyzed flow-through next was bound to a S-Sepharose fast flow column equilibrated with 0.1M phosphate buffer, pH 6.0. Purified non-lipidated OspC then was eluted from the S-Sepharose column using the dialysis buffer with 0.15 M NaCl added. A schematic of the purification process is shown in FIG. 4.

Figure 6:
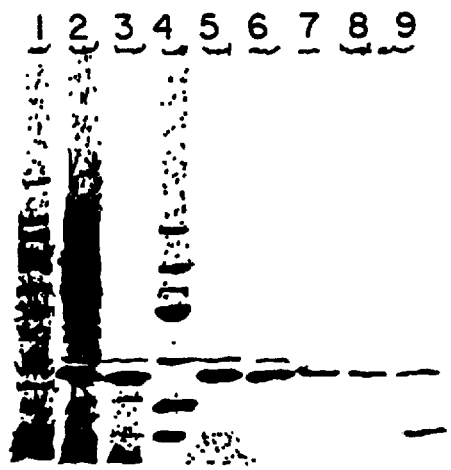
FIG. 6 shows an SDS-PAGE analysis of non-lipidated OspC produced herein at various stages of the purification procedure as described in WO 91/09870.

The aqueous solution of highly purified non-lipidated OspC was analyzed by Coomassie stained gels (FIG. 6). The purity of the product was estimated to be greater than 80%.

Example 5

Immunogenicity of Recombinant Lipidated OspC

Purified recombinant lipidated OspC, prepared as described in Example 3, was tested for immunogenicity in mice and compared to that from non-lipidated OspC prepared as described in Example 4. For this study, 4 to 8 week old female C3H/He mice were immunized on day 0 and boosted on day 21 and 42. All animals were given 1 µg each of OspC expressed from the B31 and Pko genes per dose. Both lipidated and non-lipidated forms of the antigen were tested. Formulations were tested with and without alum as an adjuvant.

Representative animals were exsanguinated on days 21, 42, 63 and 91. ELISA testing was performed on these sera using purified non-lipidated OspC as the coating antigen.

Figure 7:
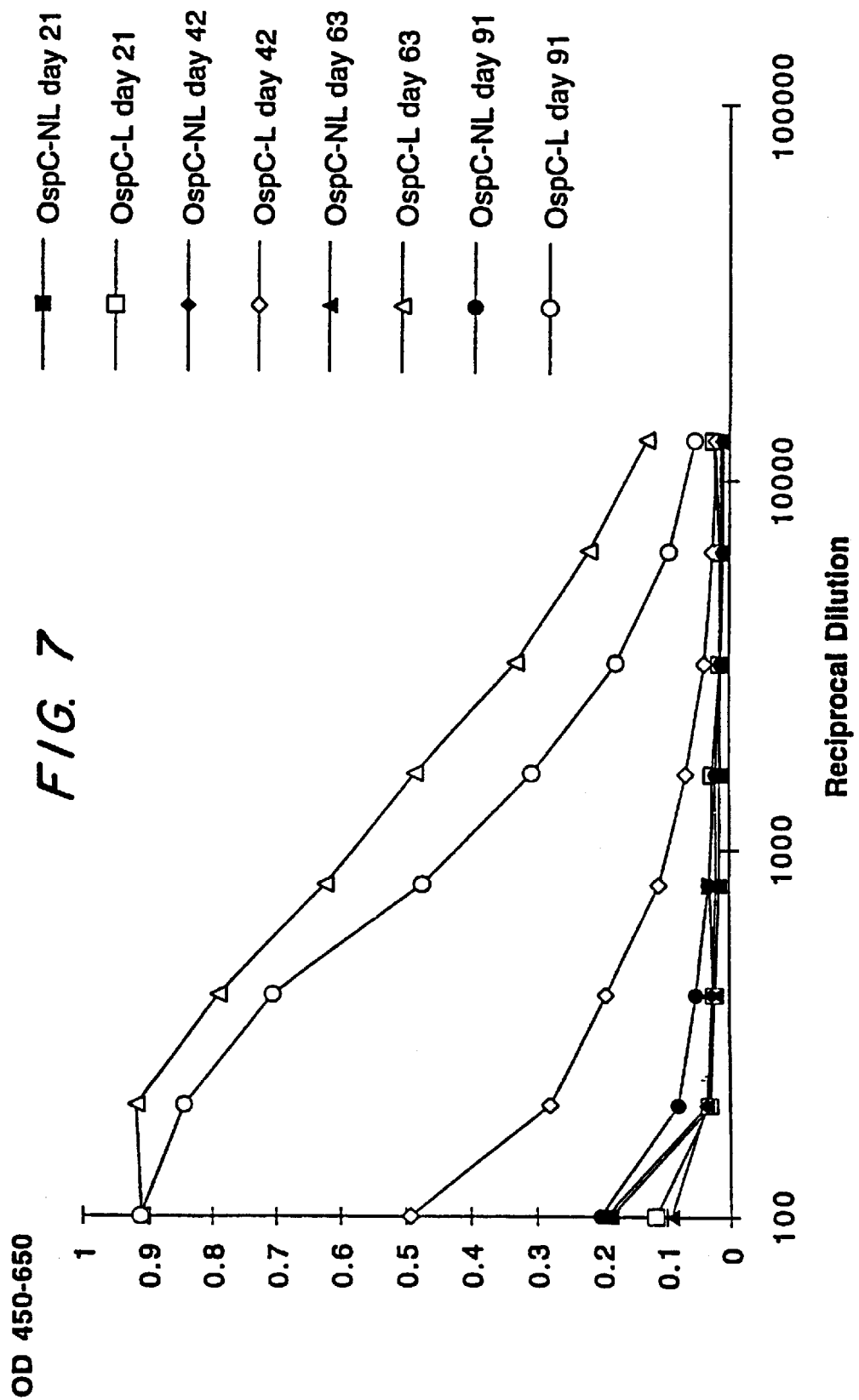
FIG. 7 is a graphical representation of the immune response of mice immunized with OspC formulations containing antigen from two OspC sub-types as measured in an anti-OspC ELISA assay.
Figure 8:
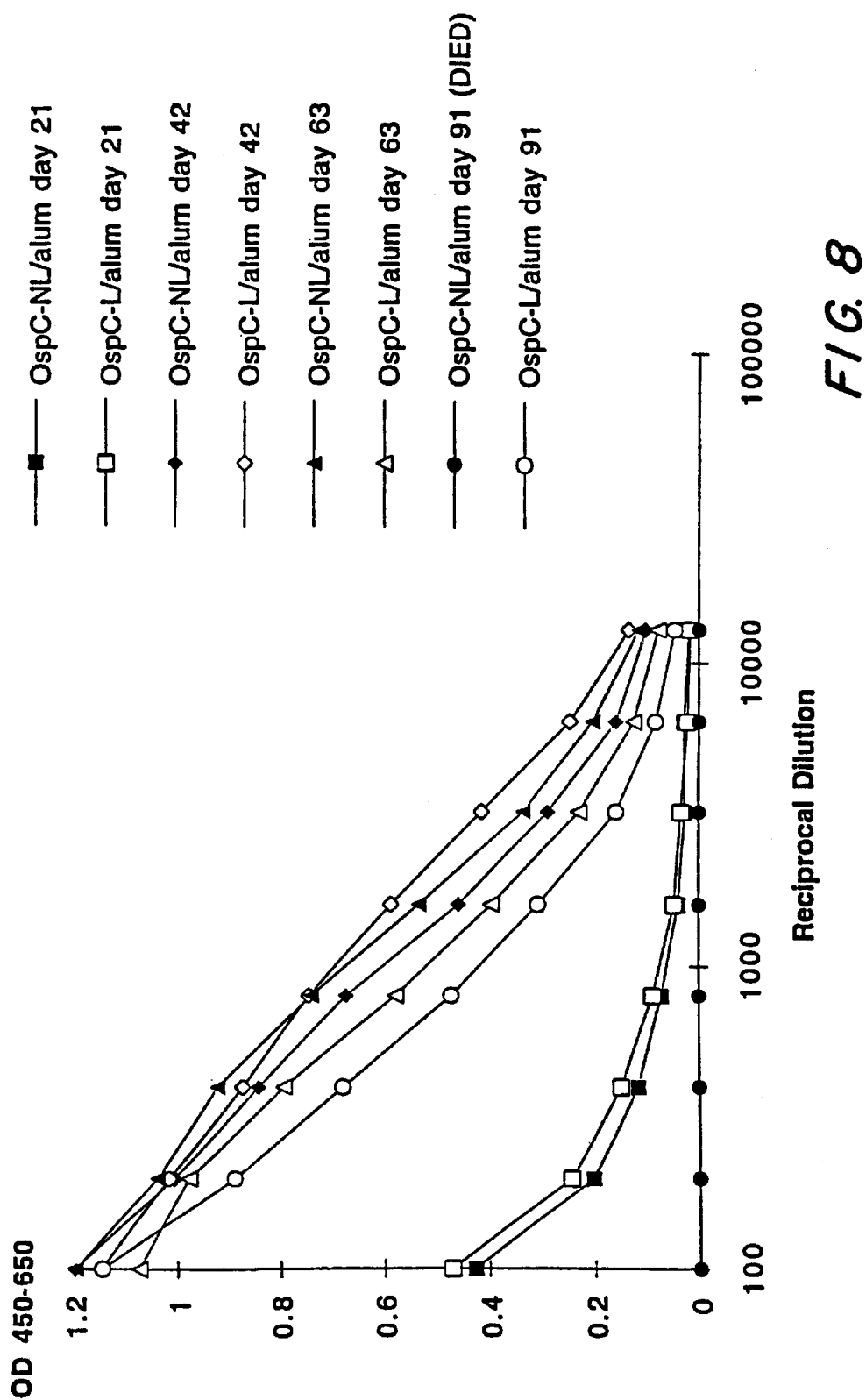
FIG. 8 is a graphical representation of the immune response of mice immunized with a two sub-type OspC formulation that contains alum adjuvant as measured in an anti-OspC ELISA assay.

The test results from mice immunized with unadjuvanted antigen (FIG. 7) show that only animals immunized with the lipidated antigen make a detectable ELISA response. However, the immune response of animals immunized antigens formulated on alum (FIG. 8) shows that two types of antigen give comparible ELISA responses and these responses develop more rapidly.

Example 6

Construction of a pET9a Expression Vector Containing a Hybrid ospA/pspA Gene Specifically designed oligonucleotide primers were used in a PCR reaction to amplify the portion of the pspA gene of interest (in this case from amino acid 1 to 321) from the *S. pneumoniae* strain RX1.

The 5'-end primer had the nucleotide sequence:
5'-GGG ACA GCA TGC GAA GAA TCT CCC GTA GCC AGT-3' (PspN1) (SEQ ID NO: 6).

The 3'-end primer had the nucleotide sequence:
5'-GAT GGA TCC TTT TGG TGC AGG AGC TGG TTT-3' (PspC370) (SEQ ID NO: 7).

The PCR reaction was as follows: 94° C. for 30 seconds to denature DNA; 42° C. for one minute for annealing DNA; and 72° C. for one minute for extension of DNA. This was carried out for 25 cycles, followed by a 5 minute extension at 72° C. This procedure introduced a stop codon at amino acid 315. The PCR product was purified using the Gene Clean II method (Bio101), and digested with SphI and BamHI.

Figure 9:
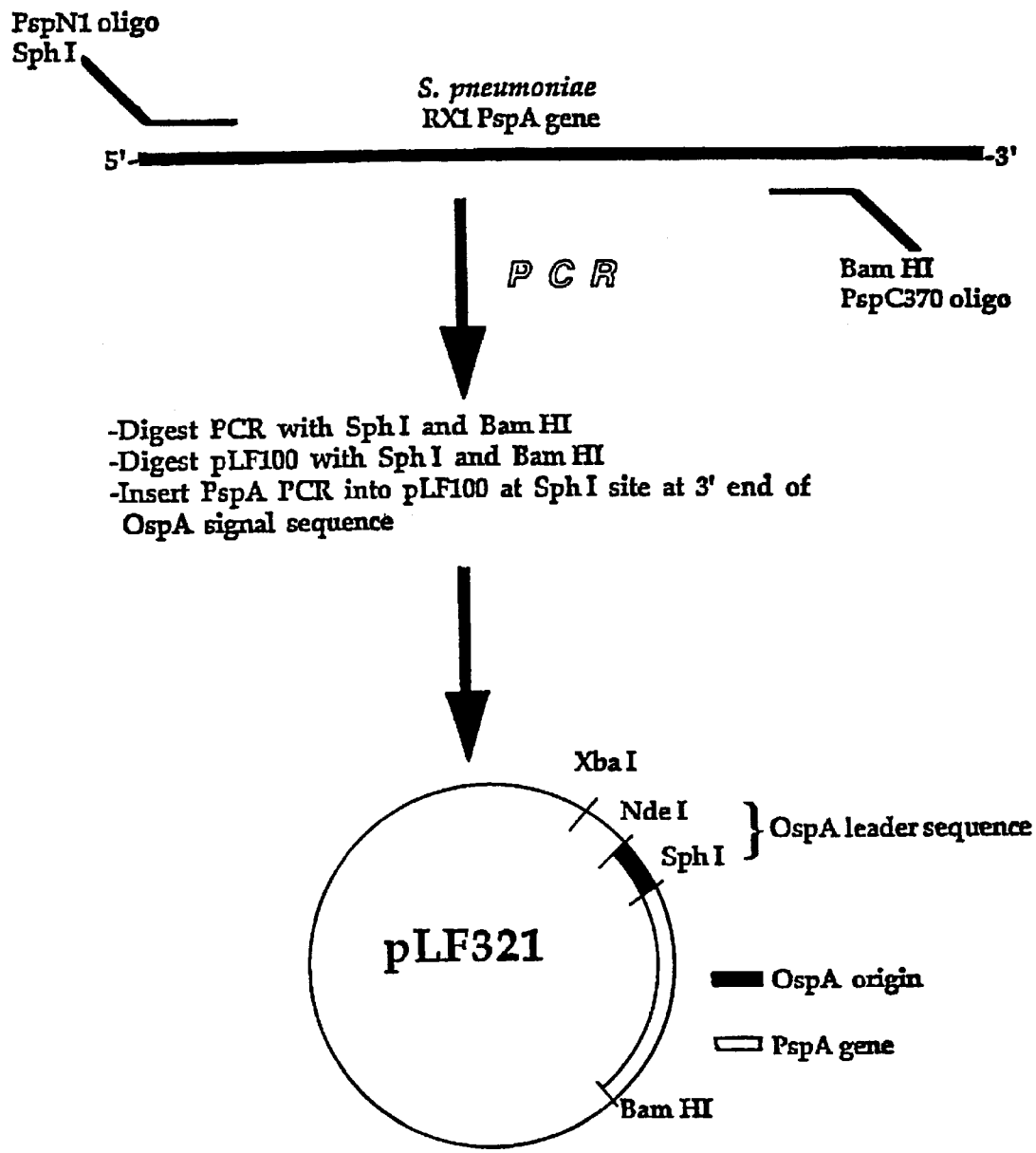
FIG. 9 is a schematic representation of a procedure for assembling plasmid vector pPA321-L.

The plasmid pLF100 (Example 1) was digested with SphI and BamHI and the amplified pspA gene was ligated to this plasmid to form the plasmid pLF321, which contained the hybrid ospA-pspA gene. The hybrid gene was excised from pLF321 by digestion with NdeI and BamHI and cloned into the NdeI and BamHI sites of the plasmid vector pET9a to place the ospA-pspA hybrid gene under the control of a T7 promoter. The resulting plasmid is called pPA321-L. This process is shown schematically in FIG. 9.

Example 7

Construction of a pET9a Expression Vector Containing the pspA Gene

Specifically designed oligonucleotide primers were used in a PCR reaction to amplify the portion of the pspA gene of interest (in this case from amino acid 1 to 321) from the *S. pneumoniae* strain RX1 using plasmid pPA321-L of Example 6.

The 5'-end primer had the nucleotide sequence:
5'-GCT CCT GCA TAT GGA AGA ATC TCC CGT AGC C-3' (PspNL-2) (SEQ ID NO: 8)

The 3'-end primer had the nucleotide sequence:
5'-GAT GGA TCC TTT TGG TGC AGG AGC TGG TTT-3' (PspC370) (SEQ ID NO: 7).

Figure 10:
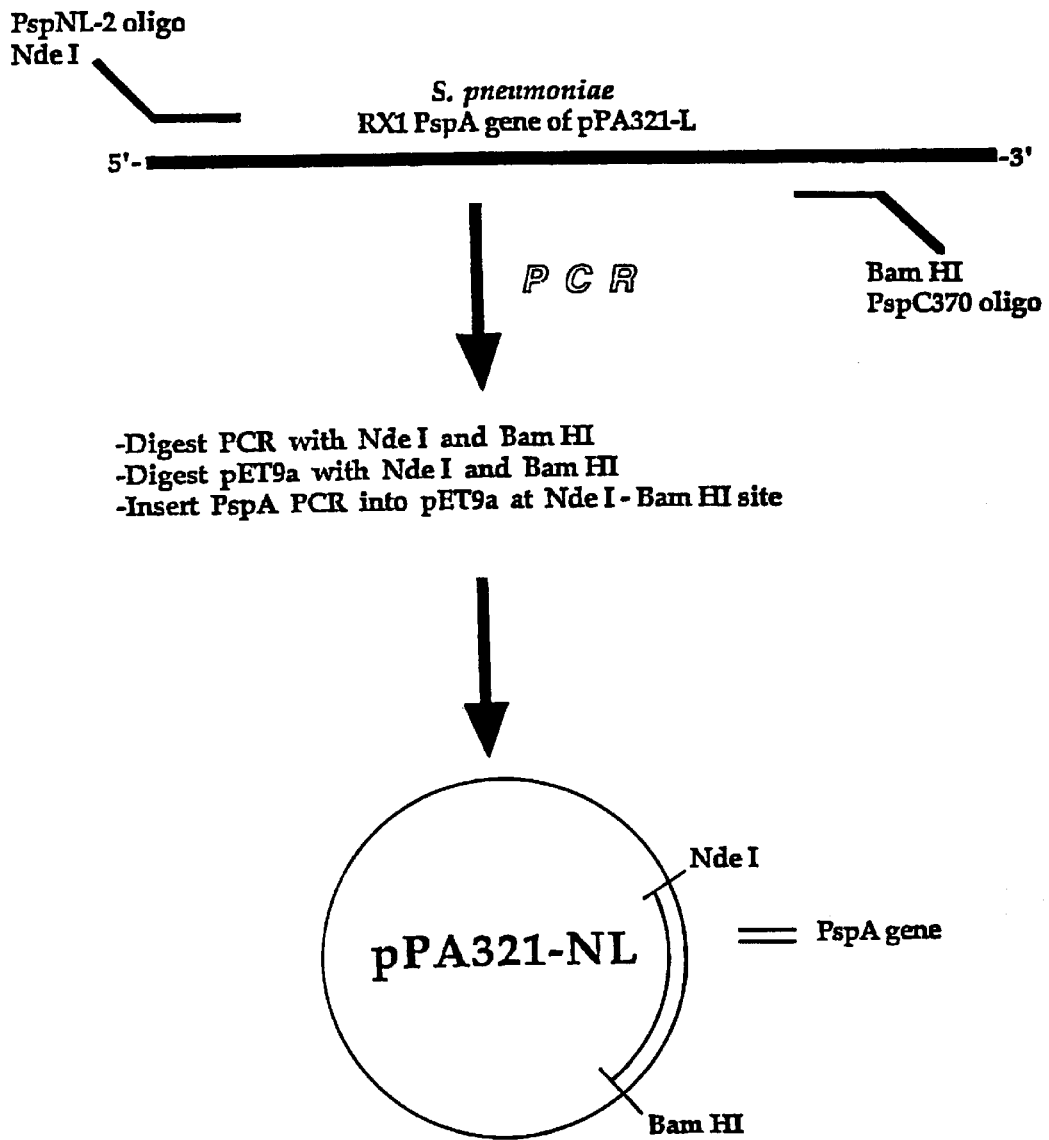
FIG. 10 is a schematic representation of a procedure for assembling plasmid vector pPA321-NL.

The PCR reaction was as follows: 94° C. for 30 seconds to denature DNA; and 72° C. for one minute for annealing and extension of DNA. This was carried out for 25 cycles, which was followed by a 5 minute extension at 72° C. This procedure introduced a stop codon at amino acid 315. The PCR product was purified using the Gene Clean II method (Bio 101), and digested with NdeI and BamHI. The digested PCR product was cloned into the NdeI and BamHI sites of the plasmid vector pET9a to place the pspA gene under the control of a T7 promoter. The resulting plasmid is called pPA321-NL. This process is shown scematically in FIG. 10.

Example 8

Expression and Purification of Lipidated PspA

Plasmid pPA321-L was used to transform *E. coli* strain BL21(DE3)pLyS. The transformed *E. coli* was inoculated into LB media containing 30 μg/ml kanamycin sulfate and 25 μg/ml chloramphenicol. The culture was grown overnight in a flask shaker at 37° C.

The following morning 50ml of overnight culture was transferred to 1 L LB media containing 30 μg/ml kanamycin sulfate and the culture was grown in a flask shaker at 37° C. to a level of OD 600 nm of 0.6–1.0, in approximately 3–5 hours. To the culture medium was added IPTG to a final concentration of 0.5 mM and the culture was grown for an additional two hours at 30° C. The cultures were harvested by centrifugation at 4° C. at 10,000×G and the cell pellet collected. Lipidated PspA was recovered from the cell pellet.

The cell pellet was resuspended in PBS at 30 g wet cell paste per liter PBS. The cell suspension was frozen and stored at −20° C. The cells were thawed to room temperature to effect lysis. DNaseI was added to the thawed material at a final concentration of 1 μg/ml and the mixture incubated for 30 minutes at room temperature, which resulted in a decrease in viscosity of the material.

The material was then chilled in an ice bath to below 10° C. and TRITON™ X-114 was added as a 10% stock solution to a final concentration of 0.3 to 1%. The mixture was kept on ice for 20 minutes. The chilled mixture was then heated to 37° C. and held at that temperature for 10 minutes. This caused the solution to become very cloudy as phase separation occurred. The mixture was then centrifuged at about 20° C. for 10 minutes at 12,000×G, which caused a separation of the mixture into a lower detergent phase, an upper clear aqueous phase and a pellet. The lipidated PspA partitioned into the detergent phase. The detergent phase was separated from the other two phases, diluted 1:10 with a buffer comprising 50 mM Tris, 2 mM EDTA, 10 mM NaCl pH 7.5, and was stored at −20° C.

Figure 11:
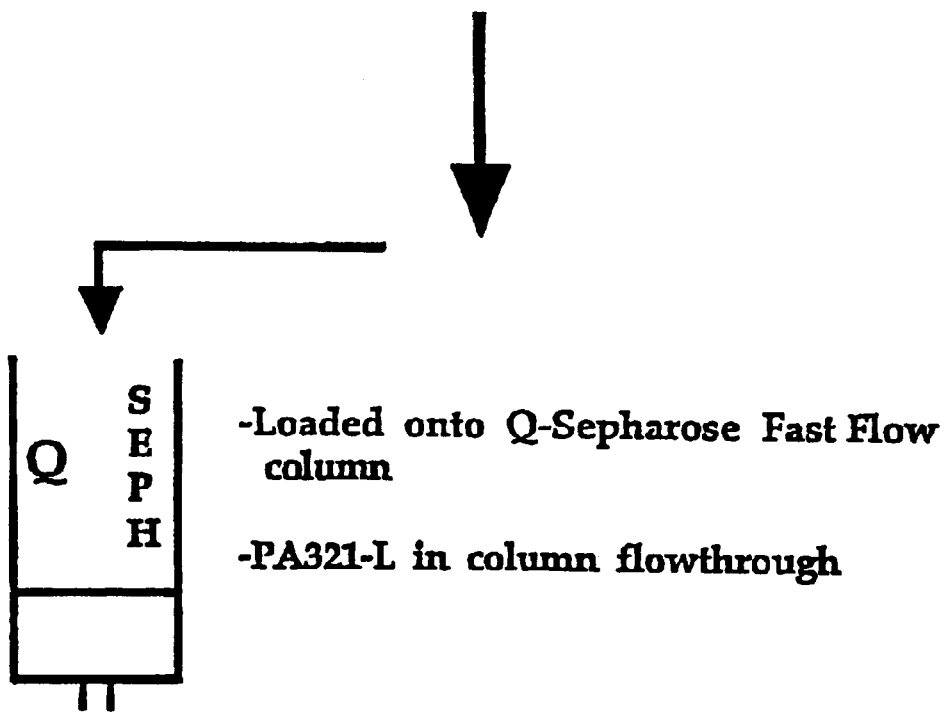
FIG. 11 is a schematic representation of the procedure employed for the isolation and purification of lipidated PspA.
Figure 14:
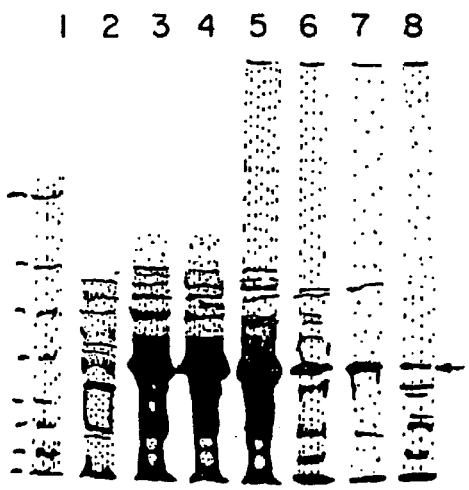
FIG. 14 shows an SDS-PAGE analysis of non-lipidated PspA produced herein at various stages of the expression and host cell fractionation procedure illustrated schematically in FIG. 12.
Figure 15:
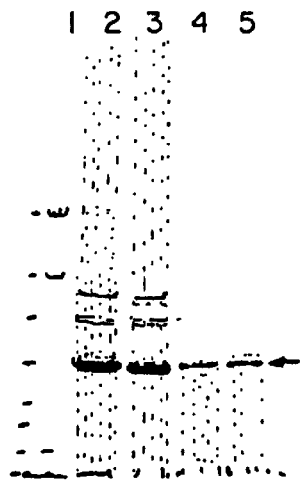
FIG. 15 shows an SDS-PAGE analysis of the PspA column chromatography results illustrated schematically in FIGS. 11 and 12.

A Q-Sepharose column was prepared in a volume of 1 ml per 5 ml diluted detergent phase. The column was washed with 2 column volumes of a buffer comprising 50 mM Tris, 2 mM EDTA, 0.3% TRITON™ X-100, 1M NaCl pH 4.0, and then equilibrated with 5 to 10 column volumes 50 mM Tris, 2 mM EDTA, 0.3% TRITON™ X-100, 10 mM NaCl pH 4.0. The pH of the diluted detergent phase material was adjusted to 4.0, at which time a precipitation occurred. This material was passed through a 0.2 μM cellulose acetate filtering unit to remove the precipitated material. The filtered diluted detergent phase was applied to the Q-Sepharose column and the flow through (containing PA321-L) was collected. SDS-PAGE analysis of this step is shown in FIG. 15. The column was washed with 1–2 column volumes of 50 mM Tris, 2 mM EDTA, 0.3% TRITON™ X-100, 10 mM NaCl pH 4.0, and the flow through was pooled with the previous flow through fraction. The pH of the flow through pool was adjusted to 7.5. The bound material, contaminating *E. coli* proteins, was eluted from the Q-Sepharose with 2 column volumes of 50 mM Tris, 2 mM EDTA, 0.3% TRITON™ X-100, 1M NaCl pH 4.0. A schematic of the purification process described in this Example is shown in FIG. 11.

Example 9

Expression and Purfication of Non-lipidated PspA

Plasmid pPA321-NL was used to transform *E. coli* strain BL21(DE3)pLyS. The transformed *E. coli* was incolulated into LB media. containing 30 μg/ml kanamycin sulfate and 25 μg/ml chloramphenicol. The culture was grown overnight in a flask shaker at 37° C.

The following morning 50 ml of overnight culture was transferred to 1 L LB media containing 30 μg/ml kanamycin sulfate and the culture was grown in a flask shaker at 37° C. to a level of OD 600 nm of 0.6–1.0, in approximately 3–5 hours. To the culture medium was added IPTG to a final concentration of 0.5 mM and the culture was grown for an additional two hours at 30° C. The cultures were harvested by centrifugaton at 4° C. at 10,000×G and the cell pellet collected. Non-lipidated PspA was recovered from the cell pellet.

The cell pellet was resuspended in PBS at 30 g wet cell paste per liter PBS. The cell suspension was frozen and stored at −20° C. The cells were thawed to room temperature to effect lysis. DNaseI was added to the thawed material at a final concentration of 1 μg/ml and the mixture incubated for 30 minutes at room temperature, which resulted in a decrease in viscosity of the material. The mixture was centrifuged at 4° C. at 10,000×G, and the cell supernatant saved, which contained non-lipidated PspA. The pellet was washed with PBS, centrifuged at 4° C. at 10,000×G and the cell supernatant pooled with the previous cell supernatant.

A MonoQ column (Pharmacia) was prepared in a volume of 1 ml per 2 ml cell supernatant. The column was washed with 2 column volumes of a buffer comprising 50 mM Tris, 2 mM EDTA, 1M NaCl pH 7.5, and then equilibrated with 5 to 10 column volumes of a buffer comprising 50 mM Tris, 2 mM EDTA, 10 mM NaCl pH 7.5. The cell supernatant pool was applied to the Q-Sepharose column and the flow through was collected. The column was washed with 2–5 column volumes of 50 mM Tris, 2 mM EDTA, 10 mM NaCl pH 7.5, and the flow through pooled with the previous flowthrough.

The elution of bound proteins began with the first step of a 5–10 column volume wash with 50 mM Tris, 2 mM EDTA, 100 mM NaCl pH 7.5. The second elution step was a 5–10 column volume wash with 50 mM Tris, 2 mM EDTA, 200 mM NaCl pH 7.5. The non-lipidated PspA was contained in this fraction. SDS-PAGE analysis of this step is shown in FIG. 15. The remaining bound contaminating proteins were removed with 50 mM Tris and 2 mM EDTA pH 7.5 with 300 mM–1M NaCl.

A schematic of the purification process described in this Example is shown in FIG. 12.

Example 10

Immunogenicity of Recombinant Lipidated PapA

Purified recombinant lipidated PspA, prepared as described in Example 8, was tested for immunogenicity in mice and compared to that from non-lipidated PspA prepared as described in Example 9. For this study, CBA/N mice were immunized subcutaneously in the back of the neck with 0.5 ml of the following formulations at the indicated PspA antigen concentrations.

| Formulation | PspA Antigen Concentration |
| --- | --- |
| Native PspA molecule of the RX1 strain (Native RX1) | 200 ng/ml |
| Non-Lipidated Recombinant PspA (pPA-321-NL) Alone in PBS* | 200 and 1000 ng/ml |
| Non-Lipidated Recombinant PspA (pPA-321-NL) Adsorbed to Alum | 200 and 1000 ng/ml |
| Lipidated Recombinant PspA (pPA-321-L) Alone in PBS | 200 and 1000 ng/ml |
| Lipidated Recombinant PspA (pPA0321-NL) Adsorbed to Alum* | 200 and 1000 ng/ml |
| Alum* | 0 ng/ml |
| PBS | 0 ng/ml |

*Alum was Hydrogel at a concentration of 200 μg/ml

Four mice were immunized on days 0 and 21 for each dosage of the formulations. The mice were then bled on day 35 and subsequently challenged with *S. pneumoniae* of A66 strain. The days of survival after challenge for the mice were recorded and surviving mice were bled on days 36, 37, 42 and 46. From these subsequent bleeds the blood was assayed for the number of colony forming units (CFU) of *S. pneumoniae*/ml. The sera taken on day 35 were assayed by ELISA for antibodies against PspA using ELISA. The days to death for the challenged mice are shown in the following table.

Survival in Immune and Non-immune CBA/N Mice

| | Immunization | | | Efficacy | | | |
| --- | --- | --- | --- | --- | --- | --- | --- |
| Group | Antigen | dose in μg | Alum | Days to Death | P value time to death* | Alive: Deed | P value Survival* |
| #1A | pPA-321-L | 1.0 | − | 4 x> 14 | 0.01 | 4:0 | 0.01 |
| #1B | PpA-321-L | 0.2 | − | 4 x> 14 | 0.01 | 4:0 | 0.01 |
| #2A | pPA-321-L | 1.0 | + | 4 x> 14 | 0.01 | 4:0 | 0.01 |
| #2B | pPA-321-L | 0.2 | + | 4 x> 14 | 0.01 | 4:0 | 0.01 |
| #3A | pPA-321-NL | 1.0 | − | 1, 1, 2, 2 | n.s. | 0:4 | n.s. |
| #3B | pPA-321-NL | 0.2 | − | 1, 1, 2, ≧15 | n.s. | 1:3 | n.s. |
| #4A | pPA-321-NL | 1.0 | + | 4 x> 14 | 0.01 | 4:0 | 0.01 |
| #4B | pPA-321-NL | 0.2 | + | 4 x> 14 | 0.01 | 4:0 | 0.01 |
| #5 | FL-Rx1 | 0.2 | − | 4 x> 14 | 0.01 | 4:0 | 0.01 |
| #6 | none | 0.0 | + | 1, 1, 3, 6 | n.s. | 0:4 | n.s |
| #7 | none | 0.0 | − | 1, 1, 1, ≧15 | n.s. | 1:3 | n.s. |
| | pooled none | 0.0 | | 5 × 1, 3, 6, ≧15 | — | 1:7 | |

Note:
*indicates versus pooled controls; time to death, by one tailed two sample rank test; survival, by one tailed Fisher Exact test. Calculations have been done using "one tail" since we have never observed anti-PspA immunity to consistently cause susceptibility.

The number of CFU in the blood of the mice are shown in the table below.

Bacteremia in Immune and Non-Immune CBA/N Mice

| | Immunitation | | | Cog₁₀ CFU | | | |
|---|---|---|---|---|---|---|---|
| Group | Antigen | dose in µg | Alum | 1 day | 2 day | 6 day | 7 day |
| #1A | pPA-321-L | 1.0 | − | ≦1.6, 1.9, 2.1, 2.5 | 4 ×≦ 1.6 | 4 ×≦ 1.6 | n.d. |
| #1B | pPA-321-L | 0.2 | − | 3 ×≦ 1.6, 1.7 | 4 ×≦ 1.6 | 4 ×≦ 1.6 | n.d. |
| #2A | pPA-321-L | 1.0 | + | 2 ×≦ 1.6, 1.7, 2.9 | 3 ×≦ 1.6, 1.7 | 4 ×≦ 1.6 | n.d. |
| #2B | pPA-321-L | 0.2 | + | 2 ×≦ 1.6, 1.7, 1.7 | 4 ×≦ 1.6 | 4 ×≦ 1.6 | n.d. |
| #3A | pPA-321-NL | 1.0 | − | ≦1.6, 1.7, d, d | d, d, d, d | d, d, d, d | d, d, d, d |
| #3B | pPA-321-NL | 0.2 | − | 2 x> 7, d, d | ≦1.6, d, d, d | ≦1.6, d, d, d | n.d., d, d, d |
| #4A | pPA-321-NL | 1.0 | + | 2 ×≦ 1.6, 6.7, >7 | 3 ×≦ 1.6, 1.7 | 4 ×≦ 1.6 | n.d. |
| #4B | pPA-321-NL | 0.2 | + | ≦1.6, 1.7, 2.1, 2.4 | 4 ×≦ 1.6 | 4 ×≦ 1.6 | n.d. |
| #5 | FL-Rx1 | 0.2 | − | 2 ×≦ 1.6, 2.6, 2.7 | 4 ×≦ 1.6 | 4 ×≦ 1.6 | n.d. |
| #6 | none | 0.0 | + | ≦1.6, 4.1, >7, d | ≦1.6, 5.1, d, d | 6.1, d, d, d | d, d, d, d |
| #7 | none | 0.0 | − | 1.7, >7, >7, d | ≦1.6, d, d, d | ≦1.6, d, d, d | n.d, d, d, d |
| | pooled none | 0.0 | | ≦1.6, 4.1, >7, >7, d | 2 ×≦ 1.6, 5.1, d, d, d, d | ≦1.6, 6.1, d, d, d, d, d | n.d, d, d, d, d, d |

Note:
1 colony at the highest concentration of blood calculated out to 47 CFU or Log 1.7. Thus "≦1.6" indicates no colonies counted. >$10^7$ indicates that the mouse was alive but the number of colonies at the highest dilution was too high to count. "d" indicates the mice had died prior to assay.

These results indicate that the recombinant protein was not protective when injected alone. The recombinant antigen adjuvanted with alum and/or PAM$_3$cys lipidation was immunogenic and protective. The native full length PspA antigen did not need an adjuvant to be protective. The CFU results indicate that mice protected by immunization cleared the challenging S. pneumoniae from the blood in two days.

ELISA analysis of sera taken on day 35 indicated that there was a good correlation between protection of the mice from S. pneumoniae challenge and the induction of measurable antibody responses. No detectable antibody reponses were observed in the sera of mice immunized with the non-lipidated antigen (pPA-321-NL) in saline or to the negative controls that did not contain PspA antigen, (as shown in the table below). Good antibody responses were detected to the Native RX1 PspA antigen and to the recombinant PspA when it was lipidated with PAM$_3$cys and/or adsorbed to alum.

ELISA Analysis of Day 35 Mouse Bera

| PspA Antigen | Alum Adsorption | PspA Dose (µg/ mouse) | Resulting OD at Indicated Dilution of the Antisera* | | | | | |
|---|---|---|---|---|---|---|---|---|
| | | | 600 | 1200 | 2400 | 4800 | 9600 | 19200 |
| pPA-321-L | No | 0.1 | 0.885 (0.082) | 0.497 (0.043) | 0.271 (0.025) | 0.146 (0.017) | 0.075 (0.012) | 0.039 (0.009) |
| pPA-321-L | No | 0.5 | 1.857 (0.060) | 1.437 (0.137) | 1.108 (0.150) | 0.750 (0.139) | 0.459 (0.092) | 0.284 (0.057) |
| pPA-321-L | Yes | 0.1 | 1.373 (0.325) | 1.048 (0.376) | 0.745 (0.362) | 0.490 (0.304) | 0.288 (0.197) | 0.171 (0.147) |
| pPA-321-L | Yes | 0.5 | 1.202 (0.162) | 0.787 (0.184) | 0.472 (0.187) | 0.296 (0.102) | 0.162 (0.061) | 0.087 (0.035) |
| pPA-321-NL | No | 0.1 | 0.022 (0.035) | 0.030 (0.060) | 0.014 (0.024) | 0.007 (0.018) | 0.006 (0.005) | 0.001 (0.001) |
| pPA-321-NL | No | 0.5 | 0.029 (0.035) | 0.014 (0.014) | 0.008 (0.007) | 0.003 (0.004) | 0.002 (0.002) | 0.002 (0.002) |
| pPA-321-NL | Yes | 0.1 | 0.822 (0.181) | 0.481 (0.166) | 0.278 (0.085) | 0.154 (0.051) | 0.082 (0.029) | 0.042 (0.015) |
| pPA-321-NL | Yes | 0.5 | 1.017 (0.139) | 0.709 (0.128) | 0.447 (0.101) | 0.253 (0.057) | 0.141 (0.034) | 0.075 (0.020) |
| Native RX1 | No | 0.1 | 1.367 (0.084) | 1.207 (0.060) | 0.922 (0.070) | 0.608 (0.077) | 0.375 (0.048) | 0.209 (0.029) |
| None | No | 0 | 0.018 (0.003) | 0.012 (0.008) | 0.009 (0.003) | 0.005 (0.002) | 0.005 (0.002) | 0.005 (0.002) |
| None | Yes | 0 | 0.013 (0.006) | 0.009 (0.008) | 0.004 (0.004) | 0.004 (0.003) | 0.001 (0.001) | 0.000 (0.000) |

*The OD is the mean of the result of the four tested animals and the standard deviation is in parentheses.

To determine whether protection was at least in part mediated by the anti-PspA antibody responses, a passive experiment was run. BALB/c mice were immunized with 0.5 μg of recombinant lipidated PspA alone or absorbed to alum, or with recombinant non-lipidated PspA adsorbed to alum on days 0 and 21; and were bled on day 35. The anti-sera were diluted 1:3 or 1:15 in saline and 0.1 ml of the dilution was injected i.p. into two mice for each dilution. A 1/3 dilution of normal BALB/c mouse serum was used as a negative control. Subsequently one hour after passive immunization, the animals were challenged i.v. with the WU2 strain of S. pneumoniae (15,000 CFU). Mice passively immunized with anti-PspA sera were protected as compared to those mice that received dilutions of normal mouse sera as shown in the following table.

Passive Protection of BALB/c to WU2

| Immunizing Formulation | | PspA Dose | Dilution | Days to Death |
|---|---|---|---|---|
| PspA Antigen | Alum | (μg/animal) | of Serum | Post challenge |
| pPA-321-L | No | 0.5 | 3 | 4, >7 |
| | | | 15 | 2, 4 |
| pPA-321-L | Yes | 0.5 | 3 | >7, >7 |
| | | | 15 | 4, >7 |
| pPA-321-NL | Yes | 0.5 | 3 | 2, 4 |
| | | | 15 | >7, >7 |
| None | No | 0 | 3 | 2, 2 |

Having thus described in detail certain preferred embodiments of the present invention, it is to be understood that the invention defined by the appended claims is not to be limited by particular details set forth in the above description, as many apparent variations thereof are possible without departing from the spirit or scope thereof.

What is claimed is:

1. An isolated hybrid nucleic acid molecule for expressing a lipidated protein, the nucleic acid molecule comprising a first nucleic acid sequence encoding a signal sequence of a Borrelia lipoprotein and a second nucleic acid sequence encoding a protein, wherein the 3' end of said first nucleic acid sequence and the 5' end of said second nucleic acid sequence do not naturally occur together, and wherein said first nucleic acid sequence is contiguous with said second nucleic acid sequence when said protein is naturally lipidated, or said first and second nucleic acid sequences are separated by one codon coding for one amino acid when said protein is not naturally lipidated.

2. The hybrid nucleic acid molecule of claim 1 wherein said signal sequence is the signal sequence of an OspA protein of a Borrelia species.

3. The hybrid nucleic acid molecule of claim 2 wherein said first nucleic acid sequence and said second nucleic acid sequence are coupled in the same translational open reading frame.

4. The hybrid nucleic acid molecule of claim 3 wherein said proteins is a PspA protein of a strain of *S. pneumoniae*.

5. The hybrid molecule of claim 4 wherein said OspA protein is that of a strain of *B. burgdorferi*.

6. The hybrid molecule of claim 5 wherein said strain of *B. burgdorferi* is selected from the B31, ACA1 and Ip90 families of strains.

7. A hybrid nucleic acid molecule, comprising a first nucleic acid sequence encoding a PspA protein of a strain of *S. pneumoniae* and a second nucleic acid sequence encoding a signal sequence of an expressed protein heterologous to PspA and coupled in the same translational open reading frame as said first nucleic acid sequence.

8. An expression vector containing the hybrid nucleic acid molecule of claim 1 under control of a promoter for expression of said protein.

9. The expression vector of claim 8 wherein said protein is a PspA lipoprotein of a strain of *S. pneumoniae*.

10. An expression vector containing the hybrid nucleic acid molecule of claim 7 under control of a promoter for expression of said PspA protein.

* * * * *

SEQUENCE LISTING

<160> NUMBER OF SEQ ID NOS: 8

<210> SEQ ID NO 1
<211> LENGTH: 17
<212> TYPE: PRT
<213> ORGANISM: B. burgdorferi
<220> FEATURE:
<223> OTHER INFORMATION: leader amino acid sequence for ACA strain

<400> SEQUENCE: 1

Met Lys Lys Tyr Leu Leu Gly Ile Gly Leu Ile Leu Ala Leu Ile Ala
 1               5                   10                  15

Cys

<210> SEQ ID NO 2
<211> LENGTH: 51
<212> TYPE: DNA
<213> ORGANISM: B. burgdorferi
<220> FEATURE:
<223> OTHER INFORMATION: DNA encoding leader amino acid sequence for ACA
      strain

<400> SEQUENCE: 2
atgaaaaaat atttattggg aataggtcta atattagcct taatagcatg c          51

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: 5'-end PCR
      primer for portion of ospC gene of Pko strain of
      B. burgdorferi

<400> SEQUENCE: 3
ggcgcgcatg caataattca gggaaagg                                    28

-continued

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: 5'-end PCR
      primer for portion of ospC gene of B31 strain of
      B. burgdorferi

<400> SEQUENCE: 4
ggcgcgcatg caataattca gggaaaga                                        28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: 3'-end PCR
      primer for portion of ospC gene of B31 & Pko
      strains of B. burgdorferi

<400> SEQUENCE: 5
cgcggatcct taaggttttt ttgg                                            24

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: 5'-end PCR
      primer for portion of pspA gene of S. pneumoniae
      strain RX1

<400> SEQUENCE: 6
gggacagcat gcgaagaatc tcccgtagcc agt                                  33

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: 3'-end PCR
      primer for portion of pspA gene for S. pneumoniae
      strain RX1

<400> SEQUENCE: 7
gatggatcct tttggtgcag gagctggttt                                      30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: 5'-end PCR
      primer for portion strain RX1 pspA gene encoding
      aa's 1-321 of S. pneumoniae

<400> SEQUENCE: 8
gctcctgcat atggaagaat ctcccgtagc c                                    31
```